United States Patent
Willson et al.

(10) Patent No.: US 9,637,714 B2
(45) Date of Patent: May 2, 2017

(54) DIFFUSE LIGHT EXTENDED SURFACE AREA WATER-SUPPORTED PHOTOBIOREACTOR

(75) Inventors: Bryan Willson, Fort Collins, CO (US); Guy Babbitt, Colorado Springs, CO (US); Christopher Turner, Windsor, CO (US); Peter Letvin, Fort Collins, CO (US); Kristina Weyer-Geigel, Fort Collins, CO (US); Anna Ettinger, Thornton, CO (US); Amy Boczon, Fort Collins, CO (US); Nicholas Rancis, Fort Collins, CO (US); James Murphy, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 2864 days.

(21) Appl. No.: 11/871,728

(22) Filed: Oct. 12, 2007

(65) Prior Publication Data

US 2008/0160591 A1 Jul. 3, 2008

Related U.S. Application Data

(60) Provisional application No. 60/894,082, filed on Mar. 9, 2007, provisional application No. 60/878,506, filed
(Continued)

(51) Int. Cl.
*C12M 1/36* (2006.01)
*C12M 3/00* (2006.01)
(Continued)

(52) U.S. Cl.
CPC ............ *C12M 21/02* (2013.01); *C12M 23/06* (2013.01); *C12M 23/26* (2013.01); *C12M 23/34* (2013.01);
(Continued)

(58) Field of Classification Search
USPC .... 435/286.1, 132, 134, 252.1, 257.1–257.6, 435/286.6, 292.1–293.3, 296.1; 47/1.4
See application file for complete search history.

(56) References Cited

U.S. PATENT DOCUMENTS

| 2,732,663 A | 1/1956 | Dewey, II |
| 3,955,317 A | 5/1976 | Gudin |

(Continued)

FOREIGN PATENT DOCUMENTS

| GB | 2235210 | * | 2/1991 |
| WO | WO2006/020177 | * | 2/2006 |

OTHER PUBLICATIONS

Chapter I International Preliminary Report on Patentability for PCT/US2006/033252, filed Aug. 24, 2005, mailed Mar. 6, 2008.
(Continued)

*Primary Examiner* — Michael Hobbs
*Assistant Examiner* — Liban Hassan
(74) *Attorney, Agent, or Firm* — Faegre Baker Daniels LLP

(57) ABSTRACT

A scalable photobioreactor system for efficient production of photosynthetic microorganisms such as microalgae and cyanobacteria is described. In various embodiments, this system may include the use of extended surface area to reduce light intensity and increase photosynthetic efficiency, an external water basin to provide structure and thermal regulation at low cost, flexible plastic or composite panels that are joined together make triangular or other shapes in cross-section when partially submerged in water, use of positive gas buoyancy and pressure to maintain the structural integrity of the photobioreactor chambers and use of structure to optimize distribution of diffuse light. Other embodiments concern air tubes comprised of plastic film at the bottom of each photobioreactor chamber to provide sparging air bubbles to the chamber. The photobioreactor system design also com-
(Continued)

Figure 1:
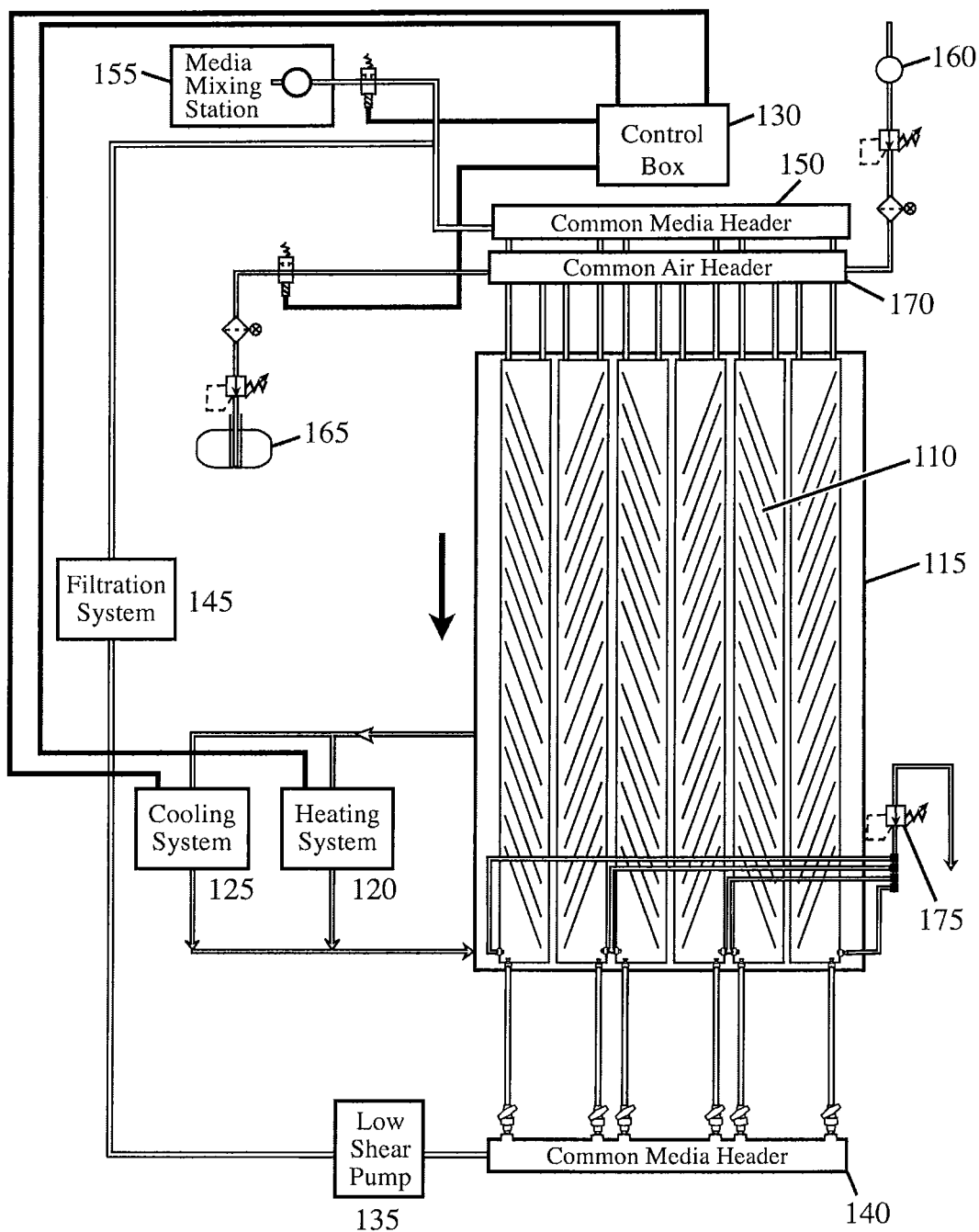

prises gas exchange, temperature control, air pumping, liquid pumping, filtration, media recycling and harvesting methods. For biofuels production, the photobioreactor system can comprise a separate growth photobioreactor and secondary stress reactor.

12 Claims, 14 Drawing Sheets

Related U.S. Application Data on Jan. 3, 2007, provisional application No. 60/877,997, filed on Dec. 28, 2006.

(51) Int. Cl.
| | |
|---|---|
| C12P 7/00 | (2006.01) |
| C12M 1/00 | (2006.01) |
| C12M 1/12 | (2006.01) |
| C12M 1/26 | (2006.01) |
| C12P 7/64 | (2006.01) |
| C12M 1/34 | (2006.01) |

(52) U.S. Cl.
CPC ............ *C12M 23/50* (2013.01); *C12M 23/58* (2013.01); *C12M 33/14* (2013.01); *C12M 41/10* (2013.01); *C12M 41/40* (2013.01); *C12M 43/02* (2013.01); *C12P 7/649* (2013.01); *C12P 7/6463* (2013.01); *Y02E 50/13* (2013.01); *Y02P 20/582* (2015.11)

(56) References Cited

U.S. PATENT DOCUMENTS

| | | | |
|---|---|---|---|
| 3,955,318 A | 5/1976 | Hulls | |
| 3,981,803 A | 9/1976 | Coulthard | |
| 4,149,589 A | 4/1979 | Hopman | |
| 4,201,525 A | 5/1980 | Brown et al. | |
| 4,241,724 A | 12/1980 | Hull | |
| 4,253,271 A | 3/1981 | Raymond | |
| 4,290,242 A | 9/1981 | Gregory | |
| 4,320,594 A | 3/1982 | Raymond | |
| 4,324,068 A | 4/1982 | Anthony | |
| 4,368,056 A | 1/1983 | Pierce et al. | |
| 4,390,624 A * | 6/1983 | Leavitt | ............... 435/107 |
| 4,473,970 A | 10/1984 | Hills | |
| 4,744,349 A | 5/1988 | Sorensen | |
| 4,879,232 A | 11/1989 | MacDonald et al. | |
| 4,910,912 A | 3/1990 | Lowrey, III | |
| 4,921,803 A | 5/1990 | Nohr | |
| 4,950,601 A | 8/1990 | MacDonald et al. | |
| 4,952,511 A | 8/1990 | Radmer | |
| 4,954,055 A | 9/1990 | Raible et al. | |
| 4,958,460 A | 9/1990 | Neilson et al. | |
| 4,997,347 A | 3/1991 | Roos | |
| 5,137,828 A | 8/1992 | Robinson et al. | |
| 5,250,427 A | 10/1993 | Weaver et al. | |
| 5,270,175 A | 12/1993 | Moll | |
| 5,534,417 A * | 7/1996 | Arad et al. | ............... 435/67 |
| 5,536,398 A | 7/1996 | Reinke | |
| 5,573,669 A | 11/1996 | Jensen | |
| 5,591,341 A | 1/1997 | Jensen | |
| 5,597,731 A | 1/1997 | Young et al. | |
| 5,659,977 A | 8/1997 | Jensen | |
| 5,661,017 A | 8/1997 | Donahay et al. | |
| 5,778,823 A | 7/1998 | Adey et al. | |
| 5,846,816 A | 12/1998 | Forth | |
| 5,851,398 A | 12/1998 | Adey | |
| 5,910,254 A | 6/1999 | Guelcher et al. | |
| 5,958,761 A | 9/1999 | Yogev et al. | |
| 5,981,271 A | 11/1999 | Doucha et al. | |
| 6,000,551 A | 12/1999 | Kanel et al. | |
| 6,037,416 A | 3/2000 | Iwamoto et al. | |
| 6,083,740 A | 7/2000 | Kodo et al. | |
| 6,156,561 A | 12/2000 | Kodo et al. | |
| 6,174,720 B1 | 1/2001 | Oxley et al. | |
| 6,192,833 B1 | 2/2001 | Brune et al. | |
| 6,329,196 B1 | 12/2001 | Johnson et al. | |
| 6,348,347 B1 | 2/2002 | Hirabayashi | |
| 6,370,815 B1 | 4/2002 | Skill et al. | |
| 6,395,521 B1 | 5/2002 | Miura | |
| 6,416,993 B1 | 7/2002 | Wexler et al. | |
| 6,492,149 B1 | 12/2002 | Muller-Feuga | |
| 6,524,486 B2 | 2/2003 | Borodyanski | |
| 6,579,714 B1 | 6/2003 | Hirabayashi et al. | |
| 6,602,703 B2 | 8/2003 | Dutil | |
| 6,827,036 B2 | 12/2004 | Connolly | |
| 6,858,430 B1 | 2/2005 | Reddy et al. | |
| 6,986,323 B2 | 1/2006 | Ayers | |
| 7,056,725 B1 | 6/2006 | Lu | |
| 2002/0034817 A1 | 3/2002 | Henry et al. | |
| 2002/0064470 A1 | 5/2002 | Andersen et al. | |
| 2002/0072109 A1 | 6/2002 | Bayles et al. | |
| 2002/0079270 A1 | 6/2002 | Borodyanski et al. | |
| 2002/0108582 A1 | 8/2002 | Connolly | |
| 2003/0059932 A1 | 3/2003 | Craigie | |
| 2003/0073231 A1 | 4/2003 | Dutil | |
| 2003/0180898 A1 * | 9/2003 | Bailey et al. | ............... 435/134 |
| 2003/0228684 A1 | 12/2003 | Burbidge et al. | |
| 2004/0121447 A1 | 6/2004 | Fournier | |
| 2004/0129045 A1 | 7/2004 | Lee | |
| 2004/0254559 A1 | 12/2004 | Tanaami | |
| 2005/0037480 A1 | 2/2005 | Chiuen | |
| 2005/0063250 A1 | 3/2005 | Hubbard | |
| 2005/0064577 A1 | 3/2005 | Berzin | |
| 2005/0095700 A1 * | 5/2005 | Budzowski et al. | ............... 435/325 |
| 2005/0115893 A1 | 6/2005 | Brune et al. | |
| 2005/0239182 A1 | 10/2005 | Berzin | |
| 2005/0260553 A1 | 11/2005 | Berzin | |
| 2005/0266541 A1 | 12/2005 | Dillon | |
| 2005/0269259 A1 | 12/2005 | Dunlop et al. | |
| 2005/0279095 A1 * | 12/2005 | Goldman | ............... 60/641.8 |
| 2006/0035370 A1 | 2/2006 | Lee et al. | |

OTHER PUBLICATIONS

Solix Biofuels, UNFAO, "Biofuel Production Climate Change Mitigation Global Energy Independence," Aug. 12, 2006, presented Jul. 2006 at Solar 2006 Conference, Denver, CO.

Sears, James T. et al., "Mass Cultivation of Photosynthetic Algae for Biodiesel Feedstock via Linear-Peristaltic Thermal-Regulated Aseptic Photo-Bioreactors," presented Jul. 2006 at Solar 2006 Conference, Denver, CO.

Sears, Jim, "Commercial Production of Biodiesel Fuel from Algae," presented Jul. 2006 at Solar 2006 Conference, Denver, CO, SunSource Industries, Jan. 5, 2006, version 2.2.

Sears, Jim et al., Biodiesel from Algae: SunSource Business & Technology Review, SunSource Industries, CSU Engines & Energy Conversion Laboratory, Feb. 16, 2006, presented Jul. 2006 at Solar 2006 Conference, Denver, CO.

Belarbi, El Hassan et al., "A process for high yield and scaleable recovery of high purity eicosapentaenoic acid esters from microalgae and fish oil," Enzyme and Microbial Technology 26 (2000) 516-529.

Sheehan, J. et al., "A Look Back at the U.S. Department of Energy's Aquatic Species Program—Biodiesel from Algae," National Renewable Energy Laboratory, U.S. Department of Energy's Office of Fuels Development, Jul. 1998, NREL/TP-580-24190 Close-Out Report.

International Search Report for International application No. PCT/US07-87476, mailed Aug 18, 2008.

* cited by examiner

3A

3B

4A

4B

4C

10A

10B

10C

10D

13A

13B

DIFFUSE LIGHT EXTENDED SURFACE AREA WATER-SUPPORTED PHOTOBIOREACTOR

RELATED APPLICATIONS

The present application claims the benefit under 35 U.S.C. §119(e) to U.S. Provisional Patent Application Ser. Nos. 60/877,997, filed Dec. 20, 2006; 60/878,506, filed Jan. 3, 2007 and 60/894,082, filed Mar. 9, 2007, the text of each of which is incorporated herein by reference.

FIELD OF THE INVENTION

The present invention concerns methods and apparatus for economical, high-density, highly scalable closed system photobioreactors for cultivation of algae to support production of biodiesel and other biofuels. In preferred embodiments, the photobioreactor construction is designed to optimize the utilization of sunlight to support algal growth. Other embodiments concern elements of the photobioreactor system designed to optimize temperature control of the system, to maximize algal density and productivity, and to minimize the costs of photobioreactor component materials, construction and operation.

BACKGROUND

Reliance on fossil fuels to power transportation and electricity networks is causing multiple and simultaneous energy crises. Coal, oil and natural gas all contribute to global warming and climate change, while creating geopolitical instability and energy insecurity. Recently, many developed and developing countries have turned to biofuels to solve those problems.

Unfortunately, obtaining biofuels from plant sources presents its own dilemmas. Any acre seeded for energy crops is likely to supplant an acre of food crops, which in turn causes a rise in the cost of basic food staples. Agriculture utilizes a significant amount of energy, much of which is supplied in the form of fossil fuels, thus lowering the overall carbon balance of biofuel crops. In addition, the yields of most energy crops are quite small. An acre of corn produces only about 350 gallons of ethanol per year, while an acre of soy can produce about 50 gallons of biodiesel per year. Finally, use of agriculturally marginal land to grow energy crops is limited by the lack of sufficient water available to support plant growth.

A biofuel that can be grown productively on otherwise unusable land with minimal energy input is needed to convert to a sustainable energy infrastructure. No traditional land crop presents a complete solution. However, microalgae hold the promise to address each of the limiting factors of biofuels. Closed system photobioreactors can be sited on otherwise unusable land, limiting competition with food crops and minimizing water losses due to evaporation. Yields of biofuels from algae can potentially exceed the yields of soil crops by orders of magnitude (see, e.g., Natl. Renewable Energy Laboratory, "A Look Back at the U.S. Department of Energy's Aquatic Species Program: Biodiesel from Algae," NREL/TP-580-24190, July 1998). Algal cell growth can quickly replace extracted material, promising a year-round harvest. As an added bonus, the microalgae can utilize the carbon dioxide-rich flue gases of fossil-fuel power plants and other industrial exhaust gases, thus lowering the quantity of greenhouse gases expelled into the atmosphere from power plants, breweries, wineries and the like.

As of yet, there are no commercial-scale microalgae farms built for the purpose of producing biofuels. Traditional industrial photobioreactors have not yet been able to repeat the high cell densities achieved in photobioreactors on the laboratory scale. In order to produce energy crops from microalgae on a competitive basis with fossil petroleum, extremely dense cultures must be grown inside the photobioreactors, which take maximum advantage of available solar light. In addition, the materials used to build these photobioreactors must be made cost effective. Traditional closed photobioreactors, made of expensive glass and steel components and complex pumps and flow distribution systems, will not achieve biocrude cost targets that are competitive with fossil fuels. Such systems are also poorly scalable from lab bench units to commercial scale production (e.g., Grima et al., J. Applied Phycology 12:355-68, 2000). A need exists in the field for economical, efficient closed system photobioreactors that are capable of growing high density algal cultures, designed to optimize utilization of solar light, and to produce biofuels at a price point that is competitive with fossil fuels.

SUMMARY OF THE INVENTION

The present invention satisfies an unresolved need in the art by providing methods, apparatus and compositions for an economical, efficient closed system photobioreactor that is capable of growing high density algal cultures, designed to optimize utilization of solar light, and to produce biofuels at a cost that is competitive with fossil fuels. The photobioreactor can also be used to produce other products than fuel such as proteins, starch, other carbohydrates, vitamins, carotenoids, xantophylls and cellulose based materials.

Certain embodiments concern designs for an improved Diffuse Light Extended Surface Area Water-Supported photobioreactor, as discussed in detail below. The skilled artisan will realize that the designs disclosed herein may be modified to optimize particular features of the system and that all such modifications are considered within the scope of the present invention.

In various embodiments, the photobioreactor may comprise one or more closed photobioreactor chambers. Preferably, the chambers are comprised of inexpensive, flexible plastic films that may, for example, be heat welded together to form the sealed chamber(s). The method of attachment is not limiting and other known attachment methods, such as the use of adhesives, may be utilized. A variety of chamber designs are contemplated within the scope of the invention. However, in a preferred design, the chambers comprise a series of tubular structures that are joined at top and bottom to form a continuous chamber. The tubular structures may be arranged in a generally parallel array and individual tubes may be vertical or alternatively may be slanted (semi-vertical) from top to bottom. The arrangement of tubular elements and the arrangement of the chamber within the photobioreactor is preferably designed to maximize the exposure of algae in the tubes to diffused sunlight.

Alternative designs may comprise parallel sheets that are heat welded or otherwise attached to each other in a series of spot welds, that may be arranged in adjacent columns in an offset pattern. The internal space between the sheets forms channels that allow fluid and air bubble circulation around the spot welds.

In other preferred embodiments, the photobioreactor chamber may comprise one or more plastic film air tubes at the bottom of the chamber. The air tube may be designed to feed small diameter air bubbles into the algal growth medium within the chamber. The bubbles may provide multiple functions, such as continuous mixing of the contents of the chamber, providing $CO_2$ gas to support algal growth, and cleaning the plastic surfaces of the chamber to minimize algal adhesion or other biofouling. This mechanism for cleaning the chamber surfaces will also enhance light transmission through the surfaces and increase photosynthetic efficiency under ambient light conditions.

In more preferred embodiments, the photobioreactor chamber may be immersed within a water basin to provide support for the chamber structure as well as to improve thermal regulation of the fluid inside the chamber. In some embodiments, the water basin may be heated or cooled by, for example, circulating cooling water through the basin, connecting a heat pump unit to the water basin, circulating hot flue gases or hot water through the basin, or any other known method for heating or cooling liquids. In addition, the large mass of the water within the water basin will itself function as a heat sink to moderate diurnal fluctuations in temperature. In preferred embodiments the water basin itself may be enclosed within, for example, a plastic cover to reduce evaporation from the water basin.

In some embodiments the photobioreactor chamber may comprise one or more air pockets at the top of the chamber. For example, in a tubular design, a tube running along the top of the chamber and continuous with the vertically or semi-vertically arranged tubes may contain air. The air pocket may be utilized to collect oxygen that is produced by algal photosynthesis. Preferably, collected oxygen may be provided to a nearby power plant to improve efficiency of combustion, for example in an Integrated Gasification Combined Cycle (IGCC) process. The air pocket may also be used to collect excess $CO_2$ and/or other gases that may be sparged through the liquid medium in the tubes, as discussed above. In addition, the air channel at the top of the chamber will further support the structure of the chamber in the water basin by providing a buoyant force on the chamber.

Still other embodiments comprise mechanisms for pumping or otherwise circulating algae and growth medium through the photobioreactor chamber. A preferred pumping mechanism in the form of, but not limited to, a low-shear air displacement pump is described below.

In various embodiments, a number of sub-systems may be employed to continuously monitor and enhance the performance of the photobioreactor. Various internal and external conditions, such as ambient and photobioreactor chamber temperature, solar insolation, growth medium pH, algal cell density, the concentration of various nutrients and waste products in the growth medium, and any other conditions may be monitored using any known technology, such as commercially available probes, electrodes and other sensing devices and an integrated computer controller system. Preferably, continuous monitoring of photobioreactor conditions may be provided to remote locations, for example by providing real-time monitoring data on an Internet website. Feedback computer-controlled mechanisms, such as heating, cooling, shading, pH adjustment, nutrient input, $CO_2$ flow and various other support functions may be automatically adjusted or alternatively may be controlled by an operator.

Algae containing lipids and/or carbohydrates for synthesis of biodiesel, ethanol or other biofuels may be harvested or collected from the photobioreactor by a number of alternative mechanisms. In some embodiments, a continuous flow harvesting system may be utilized in which a selected proportion of the algae in the chamber are continuously removed from the system. In other embodiments, a batch processing system may be used to collect algae. Algae may be separated from the growth medium by a variety of known techniques, such as the use of a continuous flow centrifuge and/or filtration system. In various embodiments, a high-density algal culture may be shunted to a separate chamber or pond for various treatments before harvesting. For example, the algae may be subjected to some form of environmental shock (temperature, pH, light, salinity, concentration of one or more chemicals or regulatory compounds) to increase lipid production prior to harvesting. A simple way to passively stimulate lipid production is to grow algae to the maximum cell density with pH controlled by $CO_2$ and to stop $CO_2$ control after depletion of nitrogen in the media.

Any known species of algae or photosynthetic microorganism may be grown in the photobioreactor. In preferred embodiments, *Tetraselmis suecica*, UTEX 2286 and NREL/Hawaii TETRA 01, *Tetraselmis chuii*, *Nannochloropsis oculata* UTEX 2164, CCMP 525, *Nannochloropsis* sp. UTEX 2341, *Nannochloropsis salina* NANNO 01 NREL/Hawaii, CCMP 1776, 1777, 1776, *Chlorella salina* SAG 8.86, *Chlorella prototheoides* UTEX 25, *Chlorella ellipsoidea* UTEX 20 or several strains of *Dunaliella tertiolecta* (UTEX LB999, DCCBC5, ATCC 30929) and *Dunaliella salina* may be grown, either separately or as a mixture of species. It is anticipated that different algal species may be selected for growth, depending on the ambient temperature, light intensity, altitude, season, geographical location, water salinity or other factors.

Some embodiments may concern methods, compositions and/or apparatus to convert algal components into biofuels. The present invention is not limited to any specific technique for biofuels production, but may utilize any known method for production of biofuels from lipids, carbohydrates or other components of algae. (See, e.g., U.S. Pat. Nos. 5,354,878; 6,015,440; 6,712,867; 6,768,015; 6,822,105; 6,979,426 and 7,135,308.) In an exemplary embodiment, algal triglycerides may be converted into biodiesel without the initial separation or extraction of the algal lipids, as disclosed in provisional patent application Ser. No. 60/952,443, entitled "Continuous Algal Biodiesel Production Facility," by Mark T. Machacek and Thomas Gordon Smith, filed on Jul. 27, 2007, the contents of which are incorporated herein by reference.

BRIEF DESCRIPTION OF DRAWINGS/FIGURES

The following drawings form part of the present specification and are included to further demonstrate certain aspects of the present invention. The invention may be better understood by reference to one or more of these drawings in combination with the detailed description of specific embodiments presented herein.

FIG. 1. Schematic of photobioreactor system

Figure 2:
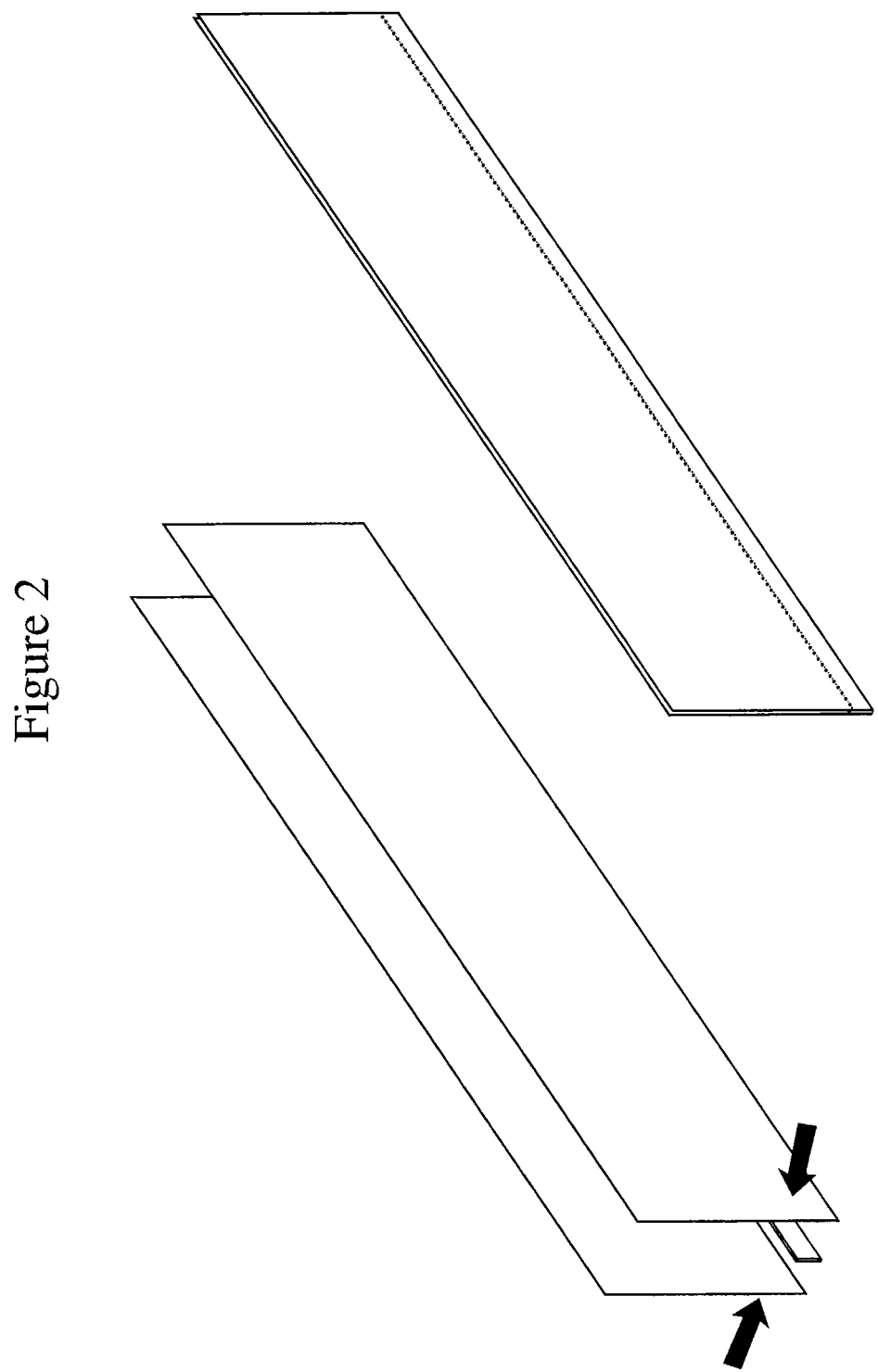

FIG. 2. Construction of photobioreactor chamber-joining two sheets of plastic film together with air tube section of plastic film.

Figure 3:
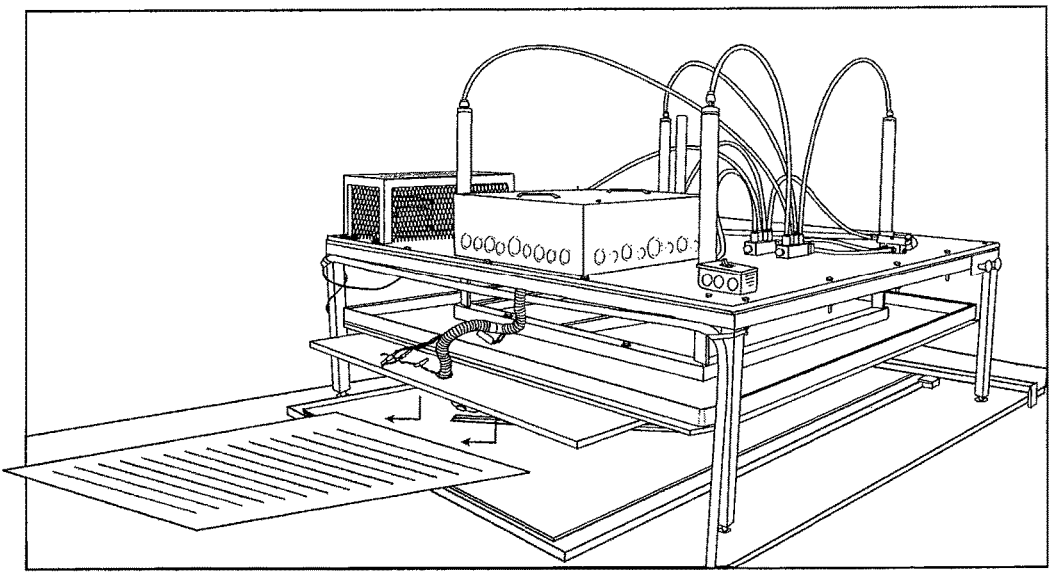
Figure 3:
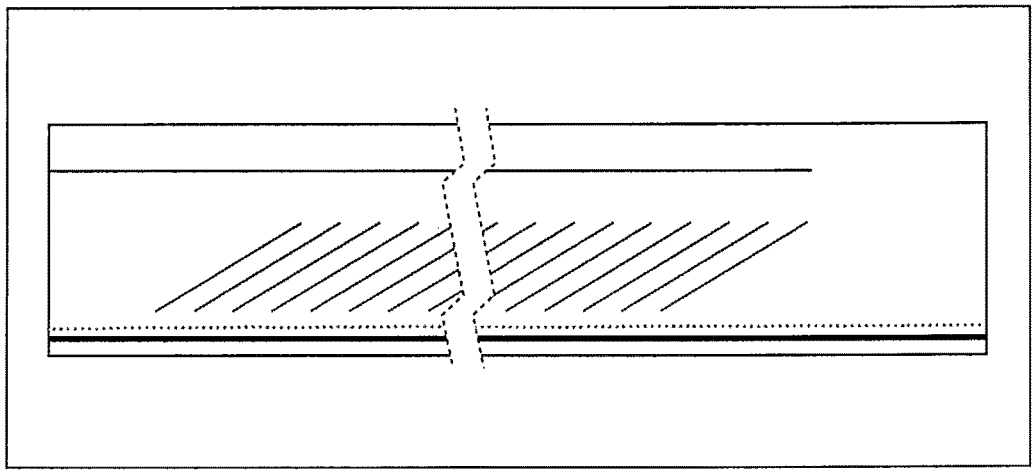

FIG. 3. (A) Tube-Welding Machine and (B) resultant welding pattern

Figure 4:
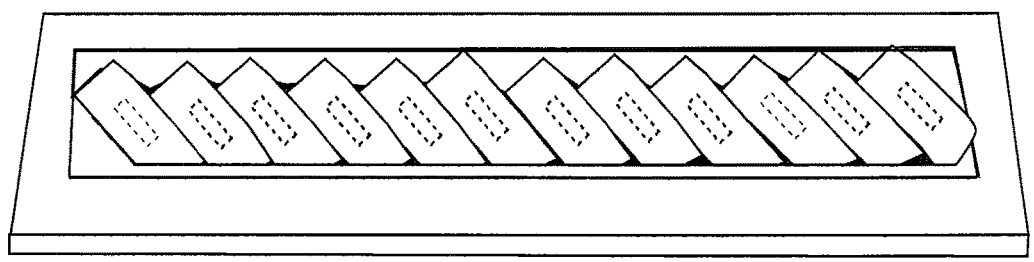
Figure 4:
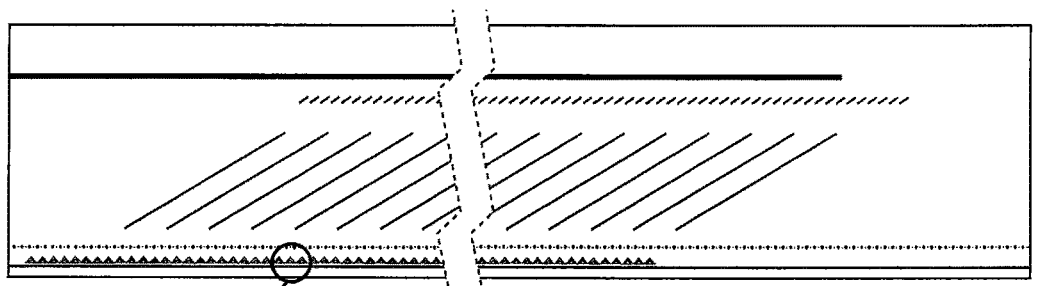
Figure 4:
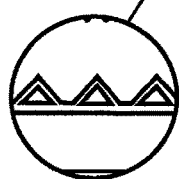

FIG. 4. (A) Zig-Zag Welding Machine, (B) resultant welding pattern and (C) enlarged section.

Figure 5:
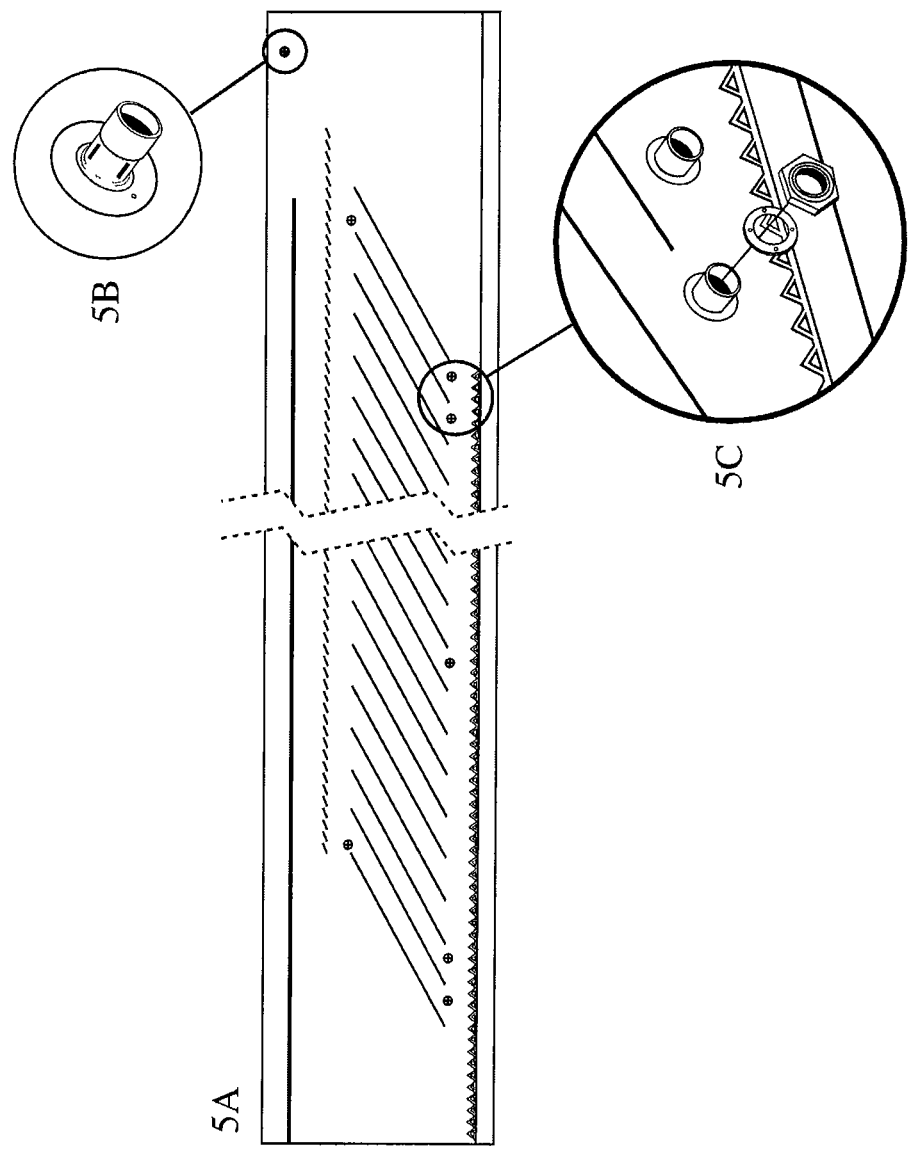

FIG. 5. (A) Bulkhead holes positions diagram, (B) plate-port closeup and (C) bulkhead closeup.

Figure 6:
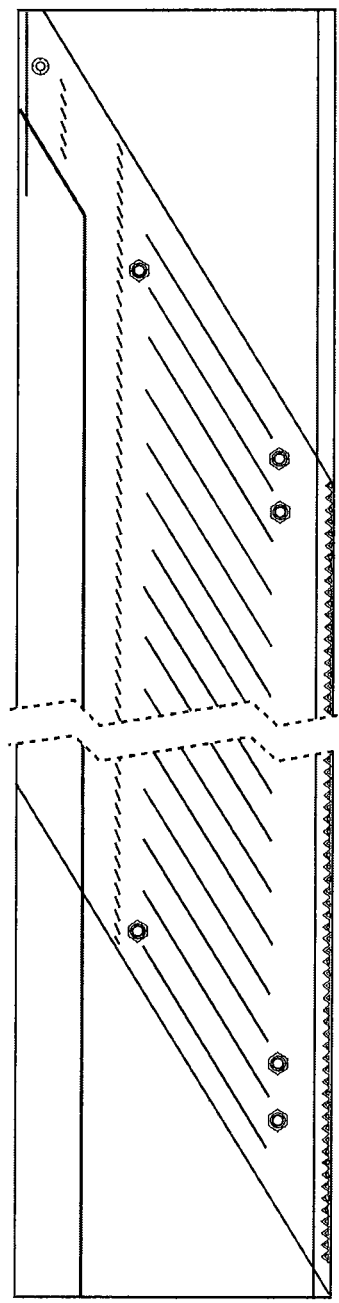

FIG. 6. Terminal ends vertical welds placement

Figure 7:
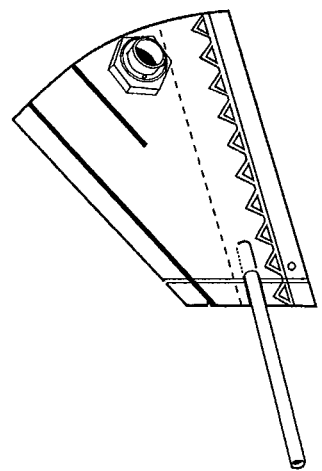
Figure 7:
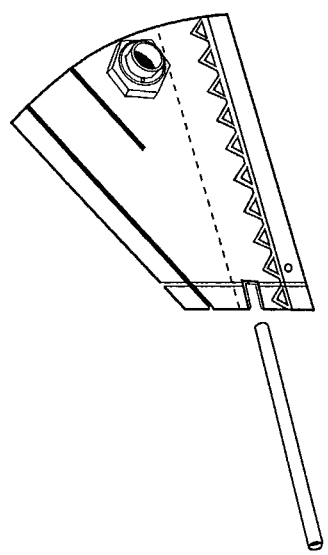

FIG. 7. Air inlet hard plastic tube and insertion procedure

Figure 8:
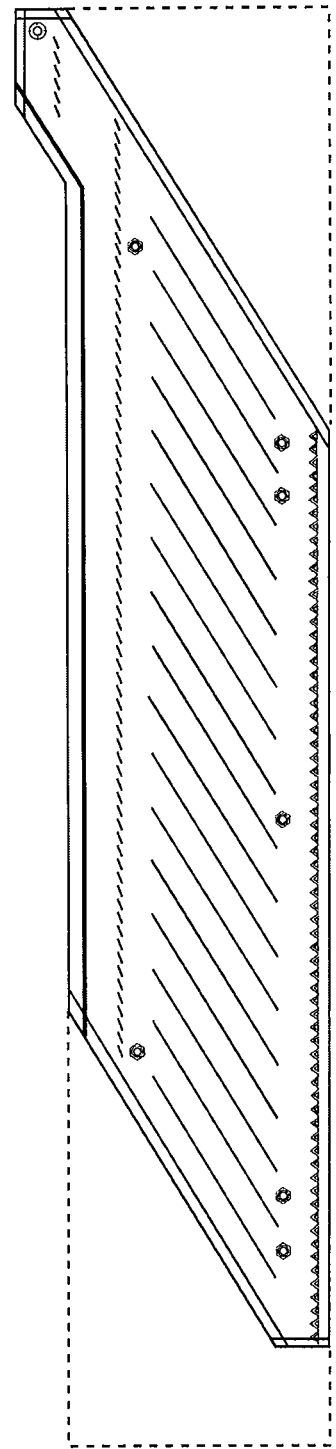

FIG. 8. Excess plastic cutoff on all four sides around photobioreactor chamber

Figure 9:
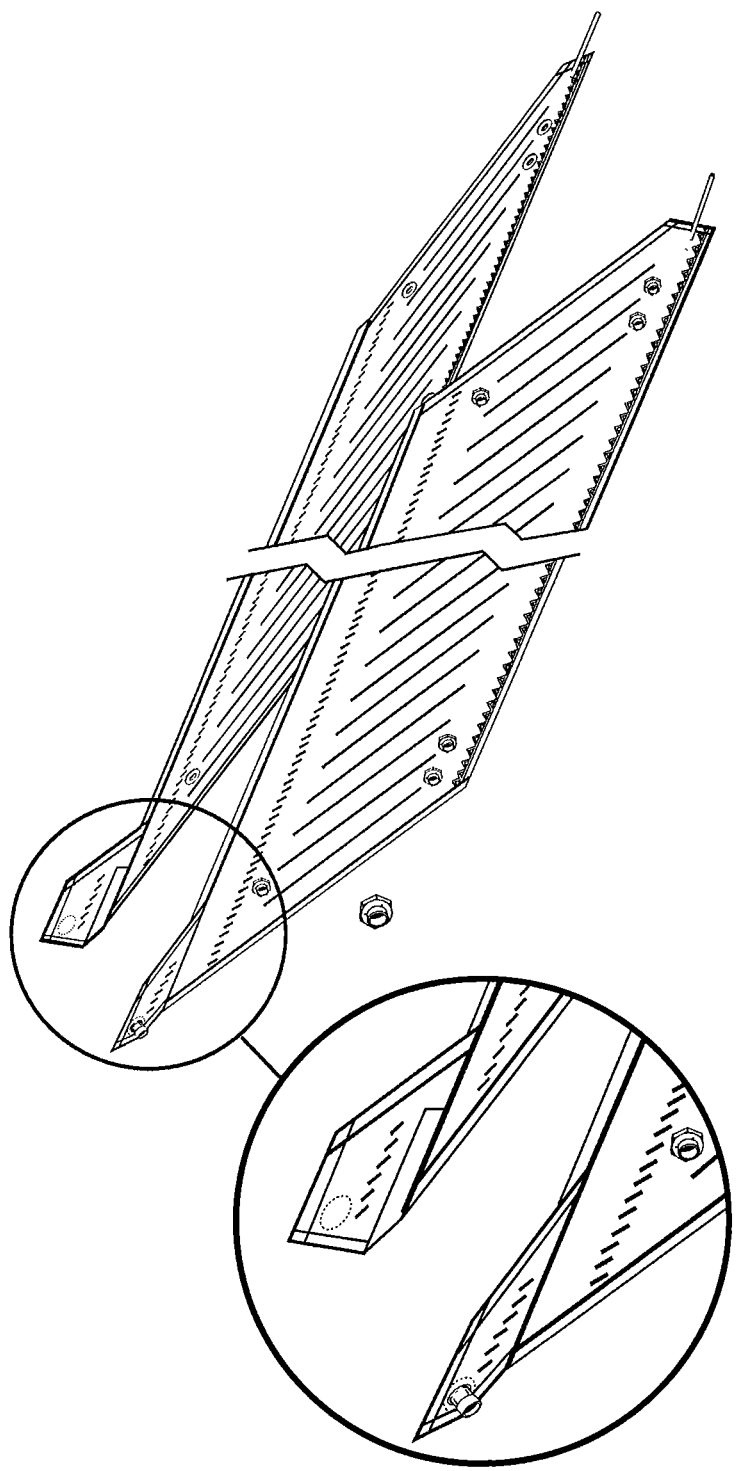

FIG. 9. Diagram of heat weld to join two bags on top

Figure 10:
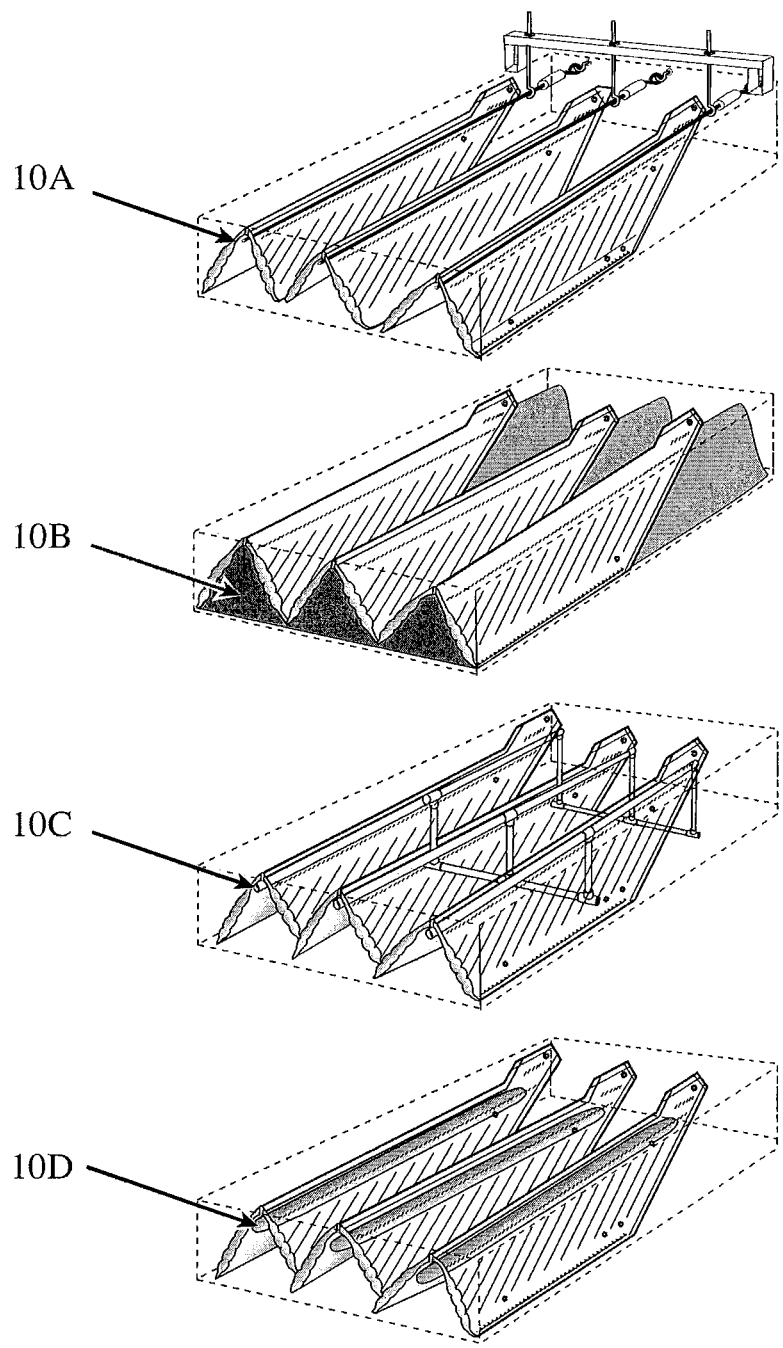

FIG. 10. Diagram of different support systems (A) wire, (B) earthen embankments, (C) internal frame, (D) balloon structure.

Figure 11:
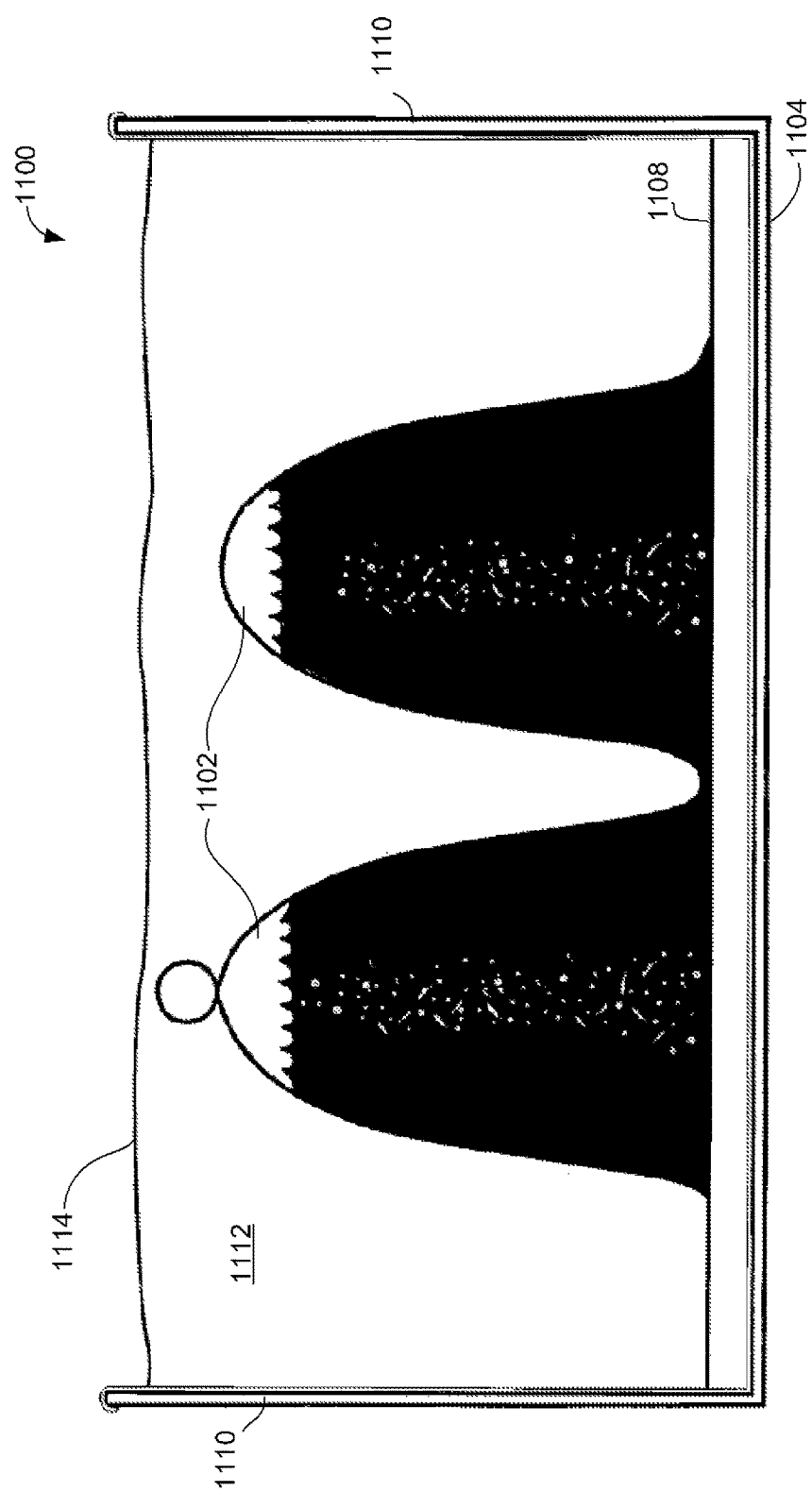

FIG. 11. Cross section of single triangular photobioreactor chamber in alternative bag design FIG. 12. Photobioreactor panel with straight tube design.

Figure 13:
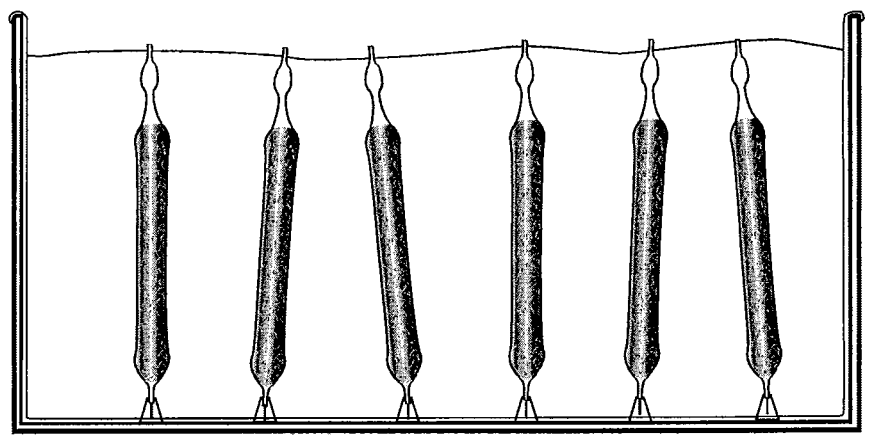
Figure 13:
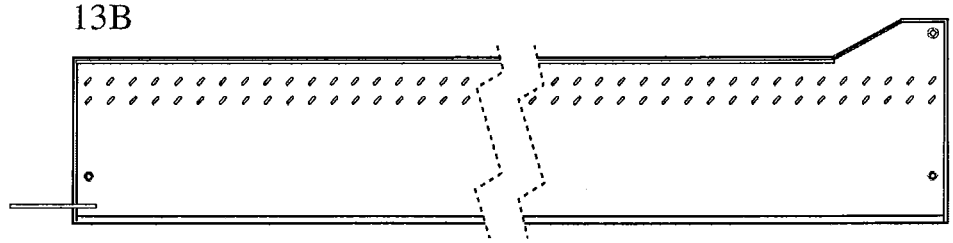

FIG. 13. (A) Cross-section of vertical photobioreactor chambers attached to the bottom of the external basin. (B) Welding diagram of vertical photobioreactor chambers that can be attached to the bottom of the external basin.

Figure 14:
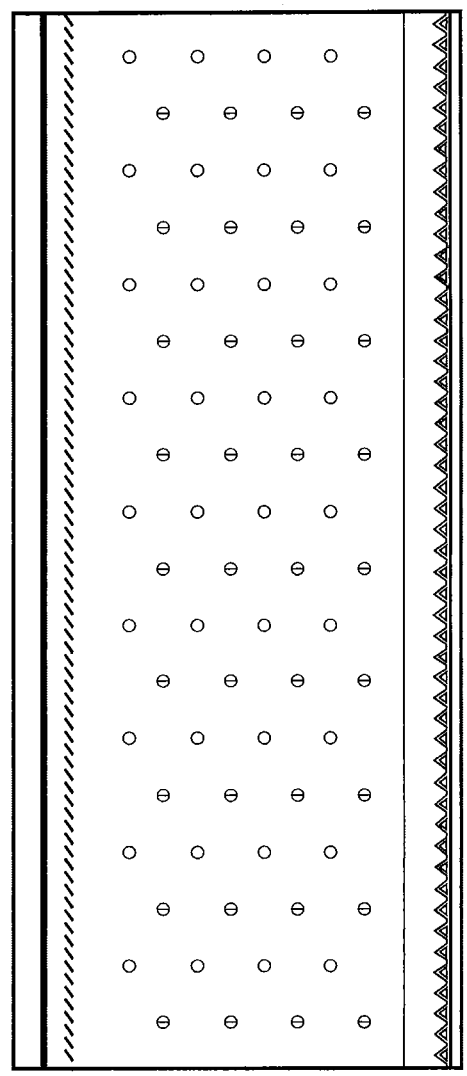

FIG. 14. Illustration of dimpled photobioreactor chamber design.

DESCRIPTION OF ILLUSTRATIVE EMBODIMENTS

Definitions

As used herein, "a" or "an" may mean one or more than one of an item.

As used herein, the terms "and" and "or" may refer to either the conjunctive or disjunctive and mean "and/or".

As used herein, "about" means within plus or minus 10% of a value. E.g., "about 100" would refer to any number between 90 and 110.

Photobioreactor

The skilled artisan will understand that methods, compositions and apparatus discussed in this and the following sections are exemplary only and are not meant to be limiting for the scope of the claimed subject matter. In particular, any dimensions, concentrations, compositions, times, temperatures and/or other numbers or values are exemplary only and it will be understood that alternative values for each may be utilized in the practice of the present invention and within the scope of the claimed subject matter.

Various embodiments of the present invention concern a highly-scalable, low-cost photobioreactor designed to grow photosynthetic microorganisms at high densities. In particular embodiments, the photosynthetic microorganisms are microalgae. High density algal culture allows the economic production of biofuels that are cost-competitive with petroleum based transportation fuels. By maximizing the surface area exposed to diffuse light, the light hitting the photobioreactor surfaces is most efficiently utilized. By immersing the entire photobioreactor chamber in a basin of water, inexpensive flexible plastics can be used and will have their structure supported by the external water and a positively buoyant air chamber inside the top of the photobioreactor chamber. By building bubble-dispensing air-spargers into the plastic film photobioreactor, turbulence is created to mix the contents of the photobioreactor chamber and to allow the maximum number of algal cells to be exposed to light.

An exemplary closed photobioreactor system is shown in FIG. 1. The closed photobioreactor chambers (110) are surrounded by a water basin (115). The water in the basin (115) may be actively heated and cooled by a heating system (120) or a cooling system (125) to maintain a certain temperature band or set point by way of the controller located in the control box (130). Actively maintaining temperature in this way may prove to be energy intensive and alternative heating and cooling mechanisms may be utilized, as discussed below. The photosynthetic microorganisms inside the photobioreactor chambers (110) may be circulated through the photobioreactor chambers by using a low shear pump (135). The fluid in the multiple photobioreactor chambers all flow into a common header (140) that feed the inlet of the low shear pump by way of gravity. The outlet of the low shear pump then directs the fluid through a filtration system (145). At this location, metabolites, bacteria, etc. can be removed from the algal culture in order to maintain the overall health of the culture. Before the algal culture flows into another common header (150), it passes by a junction that will supply fresh media to the algal flow by way of the media mixing station (155). This makes up for any fluid that may have been lost during the filtration process (145) in order to maintain a constant volume in the photobioreactor. The algal culture then re-enters the closed photobioreactor chambers (110). There is also a filtered source of air (160) that is combined with a filtered $CO_2$ source (165) in common air header (170). This air/$CO_2$ mixture may be fed along the entire length of the closed photobioreactor chambers (110) by way of a film tube welded into the bottom of the photobioreactor chambers. This film tube has multiple orifices that are cut or punctured into it that allow bubbles to form thereby communicating this gas mixture to the algal media. The pressure in the closed photobioreactor chambers that results from the bubbling gas is regulated by pressure regulator (175). The skilled artisan will realize that the photobioreactor system disclosed in FIG. 1 concerns a preferred embodiment and other alternative components and arrangements of the photobioreactor system may be utilized within the scope of the claimed subject matter.

Photobioreactor Chamber

The photosynthetic micro-organisms grown in this system are held inside a closed photobioreactor chamber. In preferred embodiments the chamber is comprised of two sheets of flexible plastic film that are affixed together by heat welds. This can also comprise a tube of plastic sheeting. While dimensions of the photobioreactor chamber may vary, a non-limiting example of the size of the chamber is 66 centimeters internal height and 100 meters in length. Additional details of exemplary photobioreactor chambers are provided in Example 1 below.

As discussed in Example 1, an exemplary photobioreactor chamber may comprise a series of continuous tubes, joined together at the top and bottom and arranged roughly parallel to each other. In different embodiments the tubes may be slanted at an angle to the ground, or may alternatively be approximately vertical. The chamber may also comprise an air tube at the bottom of the chamber that may be designed to provide a continuous flow of small diameter bubbles to the tubes. The bubbles preferably provide carbon dioxide to the medium and may comprise a $CO_2$ enriched gas, such as the flue gas from a power plant. The introduction of bubbles into the tubes may also serve to scrub the insides of the tubes to minimize attachment of algae or other biofilm materials that may interfere with light penetration into the growth medium.

In preferred embodiments, the chamber may be submerged in a water basin to provide improved thermal regulation and buoyant support for the structure of the chamber. Additional structural support may be provided by one or more air pockets located at the top of the chamber. Further pressure may be provided increasing the pressure inside the tubes. Air bubbles introduced at the bottom of the chamber through the air tube will rise and collect at the top of the chamber, along with oxygen that is created by photosynthesis. The air at the top of the chamber is thus oxygen enriched during daylight and may be collected and used to increase efficiency of combustion, for example in an IGCC plant. In more preferred embodiments, described in Example 1, photobioreactor chambers may be attached together in pairs. Arrangement of paired chambers at an angle to each other (FIG. 10) provides further structural support for the photobioreactor system.

Pump and Filter

When attached to the integrated photobioreactor system, the media outlet tube may be attached to a low-shear pump. Various examples of low-shear pumps are known in the art, such as air displacement pumps, diaphragm pumps, positive displacement pumps and centrifugal pumps and they may be obtained from commercial sources (e.g. Wanner Engineering, Minneapolis, Minn.; PendoTech, Princeton, N.J.; Levitronix, Waltham, Mass.; Graco, Minneapolis, Minn.).

A low-shear transverse flow membrane filter may be attached to the growth medium outlet tube of the pump. This filter separates the cells (retentate) from the growth medium (filtrate). A vacuum is created by an air pump on the filter, which pulls the growth medium into the filtration chamber. A liquid pump creates a pressure differential along the transverse axis of the filtration chamber, across which a filtration membrane is located. This provides a mechanism to create a low-shear media filtration unit that won't harm the fragile cell membranes or cell walls of the photosynthetic microorganisms being grown in the photobioreactor. Only a fraction of the growth medium may be filtered at any given time, although the system can be set to filter as much as 100 percent of the medium in a 24-hour period. The actual flow rate of the filtration unit will be set according to the allowable shear stress level of the desired species and/or strain(s) of photosynthetic microorganism to be grown in the photobioreactor, the growth rate of the particular algal species and the selected rate of harvesting of algal cells.

Once filtered out of the photobioreactor, the growth medium may be sent to a recycling chamber in which it is disinfected and sent through a filter to remove any particles that might otherwise harm culture growth. The used growth medium may be resupplied with any depleted nutrients before being added back to the photobioreactor chamber.

The entire filtration/media recycling unit is set to re-inject recycled media at the same rate that media is filtered out, thus maintaining a constant fluid level within the photobioreactor panel.

Arrangement of Photobioreactor Panels

Each photobioreactor panel described above in the Section entitled "Photobioreactor Chamber" may be attached at its top to an identical and contiguous photobioreactor panel and at the bottom to another identical and contiguous photobioreactor panel. The attached panels may then be set at an angle. Thus two panels affixed to each other at the top may resemble a triangle in cross-sectional view (FIG. 9), with the apex of the triangle being the joined tops.

The structure of the photobioreactor chamber shape may be maintained by the presence of the air pocket at the top of each photobioreactor panel, as well as through other methods of physical support, such as tension on the chamber walls provided by adjustable pressure within the chamber. One non-limiting exemplary supporting method comprises a metal wire (FIG. 10A) strung taut from one end to the other of the photobioreactor system. Another non-limiting example is to create earthen embankments upon which each panel is laid (FIG. 10B). Another non-limiting example is to place a triangular frame (FIG. 10C), comprised of metal, thermoset plastics, concrete, bricks or any other material known in the art, upon which the photobioreactor panel is laid. Another non-limiting example is to place a sealed tube (FIG. 10D), comprised of plastic sheeting and filled with air directly underneath the apex of the two photobioreactors attached at the tops.

By placing the photobioreactor panels at an angle, the effective photosynthetic surface area of the photobioreactor system is extended beyond the given amount of land upon with the system is installed. In one non-limiting embodiment, the photobioreactor panels are placed at an angle of 60 to 90 degrees from the ground, thus extending the given surface area. By extending the surface area to this extent, the photobioreactor can thus grow significantly more biomass on the same amount of land than a flat-plate reactor can grow.

One corollary of extending the surface area by angling the photobioreactor panels is that the light becomes more diffuse because it strikes the panels at a non-direct angle. This aids in the growth of microalgae, as a diffuse light system is generally more efficient than concentrated direct light for supporting photosynthesis (e.g., Alton et al., Global Change Biology, 12:776-87, 2007; Smart, J. Applied Ecology, 11:997-1006; 1974). Additionally, the phenomenon of photoinhibition, in which photosynthesis and growth are shut down in response to excess direct light, is decreased because of the diffusion of light.

Water Basin

The photobioreactor panels arranged at angles may be placed in contact with a water basin. In one non-limiting example, the photobioreactor chambers are immersed in a water basin so that the external water fills the spaces surrounding the photobioreactor panels. This external basin may serve several purposes, including temperature regulation, structural support for the photobioreactor panels or light diffusion.

As shown in FIG. 11, an external perimeter wall 1110 may surround the entire photobioreactor system to keep the external basin contained. An exemplary non-limiting material used for the perimeter wall would be rammed earth, although any other material known in the art may be used, including, but not limited to, wood, concrete, cement, bricks, thermoset plastics or metal Once the perimeter wall and basin landscaping have been completed, a bottom liner 1108 may be used to cover the entire ground surface within the photobioreactor, to prevent absorption of water from the basin into the ground. A non limiting exemplary material for this liner would be a thick plastic film, although any other known material may be used, such as concrete, cement, thermoset plastics, metal or sealed clay.

Biocidal compounds may be added to the external basin water to ensure that contaminating algal, bacterial, fungal or microbial species do not infest the external water and thus decrease its optical clarity. Alternatively, water in the external water basin may be filtered through a high-flow-rate, high-shear filtration unit to remove any contaminating microorganisms.

Temperature Control

The water in the external basin provides a thermal mass which aids the photobioreactor chamber in maintaining a constant temperature range optimal for the species and strain of photosynthetic organism being grown in the photobioreactor system. To heat the water, low-grade waste heat from a nearby industrial heat source, such as a power plant or factory, may be added to the external basin. The water may also be directly heated using an external heating system which cycles the water between the heater and the external basin. One alternative to cool the water in the basin would be to extract cold water from a pre-existing body of water such as a lake, river or ocean. As new, colder water is added to the external basin, warmer water in the basin is put back into the body of water.

A non-limiting method to both heat and cool the external basin water would be to run it through pipes which have been dug beneath the photobioreactor system at a level of between four feet and 400 feet below the ground surface. The temperature of earth within that range is normally around 57 degrees Fahrenheit. This system can be used to both cool the water on hot days and to warm it when ambient temperature becomes excessively cold. Alternatively, a heat pump could be interfaced with the photobioreactor system using the ground temperature differential as a heat sink.

As shown in FIG. 11, a top layer of plastic 1114 may be added to the photobioreactor system, covering the external basin and the photobioreactor panels. This top layer may comprise a relatively thin layer of plastic film. By adding this top layer, evaporative water losses are minimized. This top layer may comprise two layers of plastic film which are sealed together and which can be inflated with hot or cool air as a method of thermal regulation of the overall system. Additionally, this air may comprise dyes or artificial smoke that, through discoloration of the air may reduce heat transfer from the atmospheric air to the photobioreactor system.

The top layer may also be impregnated with a dye or other additive which blocks the ultraviolet portion of the light spectrum, reducing UV-induced damage to photosynthetic microorganisms and the plastic film in the photobioreactor panels. Alternatively, the top layer may comprise a coating or be impregnated with a dye or other additives that shift the wavelengths of photosynthetically inactive portions of the light spectrum (e.g. green) to photosynthetically active lightwaves (red or blue). The top layer may also comprise an additional coating or be impregnated with additives that block infrared radiation to reduce the amount of heat that enters the system from sunlight.

In certain embodiments, a system of impellers may be placed at the bottom of the water basin. A colloidal material may be added to the water and allowed to settle to the bottom of the basin. As the sun reaches its zenith, the impellers may be triggered to create turbulence in the basin water, thus suspending the colloidal material. The material then slowly flocculates so that it blocks some of the sunlight during the brightest portion of the day, thereby reducing damage to the algae or photobioreactor materials from excess direct sunlight and/or heat. This colloidal material may be comprised, for example, of a reddish clay material that mostly reflects light from the infrared portion of the light spectrum. In this way, the adverse effects of high mid-day temperatures may be minimized with a minimum input of energy.

Controls and Sensors

In preferred embodiments, a variety of sensors that monitor different environmental conditions that can impact algal growth may be located in sensor ports at each end of the photobioreactor panel. Sensors of use may include dissolved carbon dioxide sensors, dissolved oxygen sensors, fluid temperature sensors, image capture units, pH sensors, spectophotometric turbidity sensors, conductivity sensors, dissolved solids sensors and fluorometric sensors. The list of sensors is not exclusive and other sensors known in the art may be used. Such known sensors may monitor, for example, salinity or the concentrations of various ionic species, such as calcium, magnesium, phosphate, sodium, potassium, chloride, nitrate, etc.

The sensors may feed data into a central computerized control unit that provides instantaneous environmental measurements. Various inputs into the photobioreactor (such as growth medium, carbon dioxide, other nutrients, air pressure, pump flow-rate, acid or alkali solutions) may be adjusted in response to selected environmental measurements. For instance, when pH levels rise to a level of alkalinity that is not optimal for the growth of the photosynthetic organism, additional carbon dioxide can be added to the air stream to make the growth medium more acidic. Alternatively, excess acidity can be regulated by decreasing $CO_2$ input or by adding an alkali base to the medium.

Air pumped into the sealed air tube and sparged as bubbles through the photobioreactor panel may be comprised of nitrogen, ambient air, carbon dioxide, waste gases from industrial processes, combustion exhaust gases from stationary combustion chambers, power plant flue gases, or any other selected gas source. The proportion, pressure and pre-treatment of the gases may be determined by the choice of photosynthetic microorganism being grown in the photobioreactor system. Exhaust air that is pumped out of the photobioreactor panels, containing a high oxygen concentration, may be stored in external tanks. The oxygen may be collected and sold for use in other industrial processes, such as IGCC.

Alternative Photobioreactor Chamber Designs

In alternative embodiments, the photobioreactor chamber may comprise two layers of a flexible plastic, for example, polyethylene. The upper layer may be folded into a shape resembling corrugation ("accordion-style"). Each fold in the plastic is a separate photobioreactor chamber (FIG. 11). The folded top layer may be attached to the bottom layer of plastic by heat welding the two layers together, although any other method of attaching plastic sheets known in the art may be utilized. This creates, from a cutaway view, a series of protrusions attached to a bottom layer of plastic (FIG. 11). Once filled with growth medium and surrounded externally with liquid, the protrusions assume a roughly triangular shape that remains relatively rigid due to the equality of pressure in the external and internal liquid areas. Other potential shapes that can be formed, depending on the material being used and the dimensions chosen for a specific location and species are rectangular, rectilinear, trapezoidal, dome-shaped and archway-shaped. Additionally, a small air space 1102 at the top of each finger of a photobioreactor section or projection provides an upward tension to the structure, due to the buoyancy of the air pocket.

The dimensions of the photobioreactor may vary according to the environmental conditions of the specific site and the algal or cyanobacterial species chosen. The following exemplary dimensions are given for placement in a desert or other arid region where, for example, the species being grown are *Nannochloropsis* sp., *Nannochloropsis oculata*, *Nannochloropsis salina*, *Tetraselmis suecica*, *Tetraselmis chuii*, *Chlorella protothecoides* and *Chlorella ellipsoidea* and several strains of *Dunaliella tertiolecta*. Each photobioreactor chamber may have a height of 8 inches (comprising an air-gap height of 1 inch and a photobioreactor liquid height of 7 inches), a base width of 2 inches and a length of 100 meters. In this design, the welding seams of contiguous finger photobioreactors touch each other and the width tapers from two inches at the base to one inch at the top of the finger. Thus the photobioreactor chambers would resemble a triangular shape in cross-section.

Figure 12:
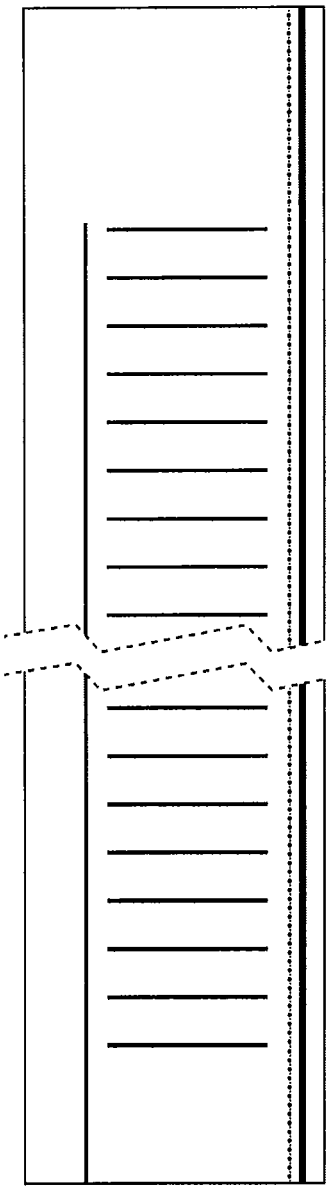

An alternative embodiment for the photobioreactor chamber design is to create vertical tube welds, instead of diagonal tube welds, as illustrated in FIG. 12. The vertical design also adds stiffness to the overall structure of the photobioreactor chamber.

Another alternative embodiment of the photobioreactor design is to create panels of plastic film photobioreactor chambers that stand upright and perpendicular to the bottom surface of the external basin. These chambers are anchored to the bottom surface through methods including but not limited to welding, weights and plastic ties. These chambers comprise two layers of plastic film joined together to make a closed compartment. The positive buoyancy of the air bubble at the top of these bags keeps them standing straight. To extend this design horizontally, more photobioreactor chambers are placed in a row, parallel to the first chamber, as shown in FIG. 13A.

One advantage of this design is that the number of welds involved is less, thus reducing the chances of weld failure, as well as reducing the costs of manufacturing. In addition to top, bottom and side welds to the panel, as well as top and bottom welds for the sparging air tube, a series of intermittent welds run the length of the bag, as shown in FIG. 13B.

Another alternative embodiment of the photobioreactor chamber design is to join two sheets of plastic film on the bottom, top and both sides and then imbue the chamber with a rigid structure through the use of alternating spot welds across the surface of the bag, creating a 'dimpled' appearance, as illustrated in FIG. 14.

Another advantage of this design is that the absence of tubular welds allows for a greater diffusion of the culture throughout the photobioreactor system. This in turn creates a healthier growing environment for the organisms.

This design would function similarly to the panels described in the first embodiment, although they would have fewer welds than the long diagonal tubes created by the design described in the first embodiment. The placement of the spot weld dimples may provide hindrance to the upward motion of the rising bubbles, thus increasing residence time of said bubbles and optimizing gas exchange or alternatively may be used to control the shape of the panels when filled with medium.

Advantages of Design During Inoculation

In conventional photobioreactor designs, the process of inoculation may encounter various problems. For example, starting the culture with a small inoculum results in a greater chance that the selected inoculated species will be outcompeted by bacteria, fungi, protozoa or other undesired algal species, or one of the most serious problems during algal propagation—photoinhibition. However starting with a large inoculum requires a very large growth photobioreactor nursery and significantly increases the cost of the system.

With a flexible photobioreactor chamber design, the photobioreactor chambers may be deflated prior to inoculation so that they take up a smaller volume. In this state, addition of a low volume of inoculum provides a proportionately greater starting concentration of desired algae in the system. As the culture grows and increases in density, additional growth medium can be added to the photobioreactor chambers. Thus the photobioreactor chambers can expand as the culture grows. In other variations, the number of photobioreactor chambers in the system may be increased as the culture grows.

This may be important during the early exponential growth phase. Biotic populations in general follow an S-curve in population growth, starting with a lag phase as they acclimate to their new environment, followed by an exponential growth phase, followed by a stationary phase where population density is maintained at a relatively constant level. During the initial lag phase and the early part of the exponential growth phase, the culture is at high risk to be outcompeted by bacteria or other unwanted species. Thus using a smaller volume reactor to begin the inoculation process and expanding the volume as the density of the culture increases may ensure that the desired species dominates the photobioreactor. Once high densities have been achieved, the risk of contamination and competition from other species is much lower. Further, the scale up in photobioreactor chamber volume as the population grows may also serve to extend the exponential growth phase and delay the onset of the stationary phase, increasing the productivity of the algal culture. Likewise, photobioreactor chambers can be added one at a time during the growth phase in order to maximize growth curves as the entire system is ramped up.

Photosynthetic Microorganisms

The photobioreactor system is designed to be non-species-dependent. The system settings, conformations, dimensions, sub-systems and contents may be adjusted to allow many types of photosynthetic microorganisms to be grown. An exemplary organism is *Chlorella protothecoides*, a non-motile green microalgae that can switch between phototrophic (photosynthetic) and heterotrophic (feeding on an external carbon source) modes. This microorganism also has the ability to accumulate large amounts of neutral lipids within its cytoplasm that can be used as a feedstock for biofuels production. However, the skilled artisan will realize that many species of algae or other photosynthetic microorganisms have been discovered and characterized and that, in alternative embodiments, any such known species may be grown in the photobioreactor to support biofuel production. Non-limiting exemplary species include *Nannochloropsis* sp., *Nannochloropsis salina, Nannochloropsis occulata Tetraselmis suecica, Tetraselmis chuii. Botrycoccus braunii, Chlorella* sp., *Chlorella ellipsoidea, Chlorella emersonii, Chlorella minutissima, Chlorella protothecoides, Chlorella pyrenoidosa, Chlorella salina, Chlorella sorokiniana, Chlorella vulgaris, Chroomonas salina, Cyclotella cryptica, Cyclotella* sp., *Dunaliella salina, Dunaliella bardawil, Dunaliella tertiolecta, Euglena gracilis, Gymnodinium nelsoni, Haematococcus pluvialis, Isochrysis galbana, Monoraphidium minutum, Monoraphidium* sp., *Nannochloris* sp., *Neochloris oleoabundans, Nitzschia laevis, Onoraphidium* sp., *Pavlova lutheri, Phaeodactylum tricornutum, Porphyridium cruentum, Scenedesmus obliquus, Scenedesmus quadricaula Scenedesmus* sp., *Skeletonema, Stichococcus bacillaris, Spirulina platensis,* or *Thalassiosira* sp.

A variety of growth media have been developed and are known in the art and in various embodiments any such known growth medium, preferably optimized for the selected species of algae or microorganism, may be utilized. In an exemplary embodiment, the growth medium used was a modified version of Guillard f/2 medium (Guillard, 1960, J. Protozool. 7:262-68; Guillard, 1975, In Smith and Chanley, Eds. *Culture of Marine Invertegrate Animals*, Plenum Press, New York; Guillard and Ryther, 1962, Can. J. Microbiol. 8:229-39), containing 22 g/L NaCl, 16 g/L Aquarium Synthetic Sea Salt (Instant Ocean Aquarium Salt, Aquarium Systems Inc., Mentor, Ohio), 420 mg/L $NaNO_3$, 20 mg/L $NaH_2PO_4 \cdot H_2O$, 4.36 mg/L $Na_2EDTA$, 3.15 mg/L $FeCl_3 \cdot 6H_2O$, 180 µg/L $MnCl_2 \cdot 4H_2O$, 22 µg/L $ZnSO_4 \cdot 7H_2O$, 10 µg/L $CuSO_4 \cdot 5H_2O$, 10 µg/L $CoCl_2 \cdot 6H_2O$, 6.3 10 µg/L $Na_2MoO_4 \cdot 2H_2O$, 100 µg/L thiamine-HCl, 0.5 µg/L biotin and 0.5 µg/L vitamin B12. This medium with an addition in some cases of $NaHCO_3$ or Tris buffer, with and without vitamins, with $KNO_3$ in some cases instead of $NaNO_3$ was used to grow a culture of *Nannochloropsis* sp., *Nannochloropsis oculata*, *Nannochloropsis salina*, *Tetraselmis suecica*, *Tetraselmis chuii*, *Chlorella salina*, and several strains of *Dunaliella tertiolecta*. Other media compositions of use for culture of algae or other microorganisms are well known but not limited in the art (see, e.g., Provasoli et al., Archiv fur Mikrobiologie 25:392-428, 1957; Harrison & Taylor, J. Phycol. 16:28-35, 1980; Keller et al., J. Phycol. 23:633-38, 1987).

Algae or other microorganisms grown in the photobioreactor may be harvested in the same unit or in a low-shear filtration unit and then transferred into a separate stress reactor that may or may not be exposed to light. Such a stress bioreactor may be placed in bags underneath the photobioreactor panels or in a separate bioreactor external to the photobioreactor system. In certain embodiments, the algae or other microorganisms may be subjected to procedures that increase lipid production, prior to harvesting and conversion into biodiesel. For example, with facultative heterotrophs such as *Chlorella protothecoides*, a carbon substrate may be added to the cells, for example ground dried corn kernels or any other non-expensive source of carbohydrates. This substrate spurs rapid neutral lipid formation within the cells, which can then be harvested for biofuels production. In other cases, the algae may be subjected to environmental stress conditions designed to enhance lipid production, such as nitrogen starvation or other nutrient deficient conditions. The amount of nitrogen in depleted media may vary from 0 to 75% of the normal amount, depending on the medium used and the type of algae to be stressed. In alternative embodiments, carbon dioxide depletion may also be used to stress algae. For different algal species, different types or combinations of stress factors may be utilized to enhance lipid production.

There are many other stress factors in addition to the nitrogen depletion or limitation, such as light, temperature, carbon dioxide, phosphates, iron, NaCl, sulfur, silica, and molybdate. Another embodiment is media recycling and replacement with growth medium that contains a limited amount of nitrogen-containing compound(s). For example the replacement growth medium could contain anywhere from 0 to 75% of the nitrogen containing compound, to induce a nitrogen-limited state for lipid production and/or storage oil accumulation.

Another way to achieve nitrogen limitation or nitrogen starvation-like conditions is to limit molybdate in the growth medium when using nitrate- ($NO_3^-$) containing compounds as a nitrogen source. $NO_3^-$ must be reduced to $NH_4^+$ in order to be assimilated into organic compounds such as amino acids. $NO_3^-$ is first converted to nitrite ($NO_2^-$) by the enzyme nitrate reductase (NR) then immediately converted to ammonia ($NH_4^+$) by the enzyme nitrite reductase (NiR). Molybdenum (Mo) is a cofactor of NR enzyme. One of the results of Mo-deficiency is reduced activity of the NR enzyme, and thus, nitrogen limitation or starvation.

A simple way to stimulate the algae to produce lipids in a bioreactor is to grow, for example, species such as *Tetraselmis suecica* or different strains of *Nannochloropsis*, which are accumulating lipids as they grow. Another simple way is to grow, for example, these species to steady state with pH controlled by $CO_2$. As soon as maximum growth is achieved, no additional $CO_2$ control should be provided, and algae produce lipids that are transferable into biodiesel. Rising of pH is an indicator of lipid production. This process can be done as a single stage batch process. Alternatively, it can also be a two-stage process with continuous or semi-continuous growth in one photobioreactor chamber, and the discontinuation of $CO_2$ addition occurring in the other photobioreactor chamber. The amount of lipids vary from 0 to 80%.

Another approach is to harvest algal biomass, dewatering the biomass by way of settling, flocculation or centrifugation, then replace the growth medium with different amounts of nitrogen or other limiting factors.

In various embodiments multiple photosynthetic species may be cultured within the photobioreactor, each of which dominates the culture when weather and environmental conditions favor its growth. For example, *Nannochloropsis* sp. or *Nannochloropsis oculata* or *Nannochloropsis salina* or *Tetraselmis suecica* or *Tetraselmis chuii*, and *Chlorella salina* may be cultured together. During summer months when solar illumination and environmental temperature are at a maximum, the *Tetraselmis* may dominate the culture. During milder fall and spring months, *Chlorella salina* cells may dominate the culture. During the cold winter months, *Nannochloropsis* ability to thrive at very low temperatures may allow it to outcompete the other species. Each species would thus be present at all times of the year, but the proportions of different species may vary seasonally.

Genetic Engineering of Algae

In certain embodiments, algae of use to produce biodiesel or other biofuels may be genetically engineered (transgenic) to contain one or more isolated nucleic acid sequences that enhance lipid production or provide other desired characteristics for algal culture, growth, harvesting or use. Methods of stably transforming algal species and compositions comprising isolated nucleic acids of use are well known in the art and any such methods and compositions may be used in the practice of the present invention. Exemplary transformation methods of use may include microprojectile bombardment, electroporation, protoplast fusion, PEG-mediated transformation of protoplasts, DNA-coated silicon carbide whiskers or use of viral mediated transformation, or vortexing protoplasts with glass beads in a solution containing the DNA to be transformed into the algal cell (see, e.g., Sanford et al., 1993, Meth. Enzymol. 217:483-509; Dunahay et al., 1997, Meth. Molec. Biol. 62:503-9; U.S. Pat. Nos. 5,270,175; 5,661,017, incorporated herein by reference).

For example, U.S. Pat. No. 5,661,017 discloses methods for algal transformation of chlorophyll C-containing algae, such as the Bacillariophyceae, Chrysophyceae, Phaeophyceae, Xanthophyceae, Raphidophyceae, Prymnesiophyceae, Cryptophyceae, *Cyclotella*, *Navicula*, *Cylindrotheca*, *Phaeodactylum*, *Amphora*, *Chaetoceros*, *Nitzschia* or *Thalassiosira*. Compositions comprising nucleic acids of use, such as acetyl-CoA carboxylase, are also disclosed.

In various embodiments, a selectable marker may be incorporated into an isolated nucleic acid or vector to select for transformed algae. Selectable markers of use may include, but are not limited to, neomycin phosphotransferase, aminoglycoside phosphotransferase, aminoglycoside acetyltransferase, chloramphenicol acetyl transferase, hygromycin B phosphotransferase, bleomycin binding protein, phosphinothricin acetyltransferase, bromoxynil nitrilase, glyphosate-resistant 5-enolpyruvylshikimate-3-phosphate synthase, cryptopleurine-resistant ribosomal protein S14, emetine-resistant ribosomal protein S14, sulfonylurea-resistant acetolactate synthase, imidazolinone-resistant acetolactate synthase, streptomycin-resistant 16S ribosomal RNA, spectinomycin-resistant 16S ribosomal RNA, erythromycin-resistant 23S ribosomal RNA or methyl benzimidazole-resistant tubulin.

Regulatory nucleic acid sequences to enhance expression of a transgene are known, such as *C. cryptica* acetyl-CoA carboxylase 5'-untranslated regulatory control sequence, a *C. cryptica* acetyl-CoA carboxylase 3'-untranslated regulatory control sequence, and combinations thereof. Additionally, promoters of alpha-tubulin genes or any other gene that is constitutively expressed from the species being worked with can be placed in front of a gene to be transformed into the algae to achieve high levels of expression.

The metabolic pathways regulating algal lipid production have not been completely characterized to date. It is clear that certain environmental conditions may trigger a switch in metabolism to enhanced lipid production. In principal, the trigger mechanism may be regulated by the activity of one or a few genes or proteins, such as transcriptional factors, protein kinases or phosphatases, receptor proteins, signal transduction proteins, hormones, cytokines, or other regulatory elements. Transformation with enzymes catalyzing rate-limiting steps in lipid synthesis, such as acetyl-CoA carboxylase, has also been suggested to enhance lipid production in algae (see, e.g., Dunahay et al., "Manipulation of microalgal lipid production using genetic engineering," in *Applied Biochemistry and Biotechnology*, Humana Press, Totowa N.J., 2007).

However, it appears that it may be more effective to change the whole cascade of enzymes involved in lipid production to create "new" algal organisms capable of producing high amounts of lipids without slowing down of the process of growth of the biomass.

Preferred Embodiments

In various embodiments, the claimed methods, compositions and apparatus may comprise:

A photobioreactor wherein an additional inlet to the ambient air stream that adds carbon dioxide or exhaust gases from an internal combustion prime mover can be opened and closed in response to the computer-controlled sensor network built into the photobioreactor system.

A photobioreactor wherein the additional carbon dioxide or exhaust gases from an internal combustion prime mover are added in response to increases in alkalinity as a means to regulate the pH level of the photobioreactor and maintain it at an optimal level for microalgae growth.

A photobioreactor wherein the additional carbon dioxide or exhaust gases from an internal combustion prime mover are added in response to the set equilibrium of dissolved carbon dioxide within the photobioreactor medium.

A photobioreactor wherein any combination of the following gases are sparged through the photobioreactor medium: power plant flue gases, carbon dioxide, ambient air, nitrogen, industrial internal combustion chamber exhaust gases and/or waste gases from other industrial bioreactors.

A photobioreactor wherein the top layer of the photobioreactor system and the top layer of the photobioreactor chambers are made of glass.

A photobioreactor wherein a fluorometric sensor is affixed within the photobioreactor chamber and chlorophyll fluorescence measurements from that fluorometric sensor are fed to a central control unit and/or distributed control units.

A photobioreactor wherein an image capture unit is affixed within the photobioreactor chamber and the images are then fed for image analysis into a central control unit and/or distributed control units.

A photobioreactor wherein a central or distributed control unit receives data from various sensors within the photobioreactor chambers and signals to a human operator or an automated feedback system to change the environmental conditions within the photobioreactor system, e.g. increasing the temperature when the photobioreactor medium gets too cold, decreasing the pH when the photobioreactor medium gets too alkaline, increasing the proportion of carbon dioxide that is sparged through the photobioreactor medium when the level of dissolved carbon dioxide becomes too low, etc.

A photobioreactor in which environmental sensors are placed throughout the photobioreactor chambers and are connected by electric wire, wireless transmitter and/or fiber optic cable and that data is fed to a central or distributed control unit A photobioreactor wherein environmental sensors are placed throughout the finger shaped photobioreactor chambers and transmit data wirelessly and that data is fed to a central control unit and/or to distributed control units.

A photobioreactor wherein temperature is regulated inside the photobioreactor chamber by removing liquid from the external water chamber, heating it or cooling it in an heat exchanger that is external to the photobioreactor system and then reintroducing it to the external water chamber.

A photobioreactor wherein temperature is regulated by pipes floating within the external water chambers through which flows a heat-exchanging fluid that has been heated or cooled by a heat exchanger that is external to the photobioreactor system.

A photobioreactor wherein temperature is regulated by pipes at the bottom of the external water chamber through which flows a heat-exchanging fluid that has been heated or cooled by a heat exchanger that is external to the photobioreactor system.

A photobioreactor wherein temperature is regulated by pipes floating within the underlying liquid-filled bag through which a heat-exchanging that has been heated or cooled by a heat exchanger that is external to the photobioreactor system.

A photobioreactor wherein excess oxygen and other waste gases are collected in the air pocket at the topmost portion of the photobioreactor chamber and is then extracted by an external air pump and stored externally for sale as high-purity oxygen.

A photobioreactor wherein media is pumped into the system and out of the system using only low-shear pumps.

A photobioreactor wherein up to 90% of the media is extracted each day or more or less often on a continual basis or a semi-continual basis in order to filter the media of biotic metabolites, foreign microorganisms and other impurities.

A photobioreactor wherein a separate media recycling system filters contaminants out of the media, kills unwanted biotic growth and adjusts metabolites to proper levels before said media is returned to the photobioreactor system.

A photobioreactor wherein an external liquid-filled bag lies underneath the photobioreactor chamber for the purposes of temperature control and creating a level surface.

A photobioreactor wherein the additional bag also serves as a secondary bioreactor into which harvested microorganisms from the photobioreactor system can be transferred and additional bag can then serve as a secondary bioreactor for heterotrophic growth of the desired microalgae or where nutrient limitation or depletion can occur to induce oil accumulation in the cells of the culture.

A photobioreactor wherein the additional bag contains chambers into which harvested microalgae from the photobioreactor system can be transferred and can then serve as a secondary bioreactor for heterotrophic growth of the desired culture, or where nutrient limitation or depletion can occur to induce oil accumulation in the cells of the culture.

A photobioreactor wherein the shape of the structures is maintained by management of hydrostatic pressure rather than on gas buouyancy.

A photobioreactor wherein each of the multiple flexible parallel tubes can be treated as a separate photobioreactor.

A photobioreactor wherein some or all of the photobioreactor chambers can be connected in series in order to increase the apparent overall length of the photobioreactor.

A photobioreactor wherein the photobioreactor chambers are connected in series can be connected via external crossover tubes or via internal passageways between the photobioreactor chambers that are adjacent or in close proximity.

A photobioreactor wherein the photobioreactor chambers are connected in parallel can be connected via an external crossover tubes and/or headers or via, internal passageways, or via internal headers.

A photobioreactor wherein culture is extracted and/or fresh media is added at specific locations along the length of the photobioreactor or at specific locations along the length of individual flexible photobioreactor tubes.

A photobioreactor wherein certain nutrients are added or added in different concentrations at specific locations along the length of the photobioreactor or at specific locations along the length of individual flexible photobioreactor tubes for the purpose of inducing nutrient stress to increase lipid content.

A photobioreactor wherein the culture is circulated through the photic zone through agitation means that do not involve air sparging.

A photobioreactor wherein fresh media is added to the culture at periodic intervals to dilute the culture and maintain constant density as the cells multiply.

A photobioreactor that comprises a growth-stage photobioreactor and a stress-stage bioreactor expressly for lipid accumulation for the production of biofuels.

A photobioreactor wherein the stress bioreactor lies adjacent to the growth photobioreactor and utilizes sunlight for autotrophic cultivation of the microalgae cells.

A photobioreactor wherein the growth and stress bioreactors comprise a single channel, separated by an filtration device and through which a pump-driven current push the algae cells through the different stages of growth and lipid accumulation so that they arrive at the terminal end of the continuous system when they are ready to be harvested.

A photobioreactor wherein the stress-stage section of the bioreactor channel lies underneath the photobioreactor section of the channel and is operated in the dark, heterotrophic mode.

A photobioreactor wherein the stress section of the bioreactor is a tower-like structure sited adjacent to the photobioreactor and operating in a dark, heterotrophic mode.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Photobioreactor Construction and Use

Photobioreactor Construction

An exemplary photobioreactor was designed and built. In an exemplary embodiment as shown in FIG. 2, a 26 centimeter high, twenty meter long sheet of plastic film was laid flat on a table. A rotary puncture device was then rolled over the mid point of the sheet across the length of the plastic sheet. This created 0.25 mm diameter holes in the plastic every 2 centimeters. The plastic sheet was then folded over in half, with the holes 5 millimeters below the fold, to form the air tube.

This air tube was then placed between two sheets of plastic film, each being 91 centimeters in height and 20 meters in length. The bottom of the air tube plastic was placed flush with the bottom of the two large sheets of plastic film.

An impulse heat welding machine specifically designed for this process was used for the next step. This machine comprised an upper and a lower platen (FIG. 3A). The upper platen moves up and down, while the lower platen remains stationary. The plastic sheets may be hand-fed into the welding machine, which welds 76 centimeters of the photobioreactor system at a time. The upper platen comprised two 69 centimeter horizontal heating elements that created the horizontal top weld, two 69 centimeter horizontal heating elements that created the horizontal bottom weld, and 5 slanted vertical heating elements that were slanted at a 31 degree angle. The bottom platen comprised corresponding heat elements that aligned with each of the above-described elements in the upper platen. This welding machine was controlled by pneumatic pistons which applied an equal pressure to the weld elements when activated. The welding machine holds that pressure for the weld duration and for a cooling period after the weld. Then the pressure was released and the platen retracted. Typical weld times were on the order of 4-10 seconds depending on the exact materials used and welder settings. In alternative embodiments, a similar machine may be designed to employ automatic rather than hand feed of the sheets.

As the machine pressed the sheets, it created a continuous horizontal heat weld across the length of the plastic film at 6.35 centimeters from the bottom of the sheets of film. An upper horizontal weld was simultaneously placed across the length of the bag at 19 centimeters from the top of the plastic sheets. The mid-sections of the plastic sheets were welded sequentially into open-ended slanted tubes using the welding machine specifically for this purpose (FIG. 3B). Comprised of 5 parallel welding elements affixed to one platen, the welding machine speeds the process of creating the photobioreactor chambers. The tube impulse welding machine formed 5 parallel slanted partial welds that did not reach either the bottom or top welds of the photobioreactor chamber. The slanted partial welds were placed 38 centimeters from the top of the plastic sheets and 18 centimeters from the bottom of the plastic sheets. The tube welds were placed at an angle of 31 degrees. A total of 26 presses were made with this heat welding machine, to create a total of 130 welds over the 20 meter length of the photobioreactor chamber.

A total of 130 tubes were thus created using the welding machine, which in turn were comprised of 130 tube welds. An additional 2 tubes were created when the terminal vertical ends of the photobioreactor were added. Thus, in an exemplary embodiment, a 20 meter long photobioreactor chamber was comprised of 132 slanted tubes.

To provide optimal shape of the reactor when filled and pressurized, a zig-zag welding machine (FIG. 4A) was used to weld a 3-centimeter high zig-zag weld across the length of the exterior plastic sheets and the air tube. An initial "zig" weld was made across the length of the photobioreactor chamber. The top of this "zig" weld started at 7.6 centimeters from the bottom of the plastic sheets and terminated at 6.6 centimeters from the bottom of the plastic sheets. The bag was then turned over and the same weld was run over the same length in the opposite direction, creating a "zag" pattern overlaying the "zig" pattern. Once completed, they resemble a zig-zag pattern (FIG. 4C). To make this weld, the operator should exert the appropriate pressure for 4-10 seconds depending on the material used and other conditions, followed by an equivalent amount of time of contact with the plastic with the same amount of pressure applied.

Alternatively the zig-zag pattern can be created using a constant temperature welder with the zig-zag or similar pattern machined, or formed, into the welding head. FIG. 4A shows an example of this.

The zig-zag welding machine was then applied to make only a "zig" pattern of welds across the length of the bag at 28 centimeters from the top of the plastic sheets. This weld was not continuous and therefore allowed air and liquids to pass through the spaces between the welds, but it provided structural support to the upmost air pocket in the photobioreactor chamber. Seven plastic bulkhead fitting holes were then cut in the photobioreactor at the positions illustrated in FIG. 5A. Each bulkhead (FIG. 5C) had an internal diameter of 32 millimeters.

The plastic bulkheads (FIG. 5C) were then fitted to the photobioreactor chamber. The bulkhead was placed inside the photobioreactor chamber with the threaded section emerging on the exterior. The hard washer with its soft-side facing the plastic was placed over the threaded section. The plastic nut was then screwed tightly over the threads. A cap was placed onto the opening to ensure that dust and microbes do not enter the bulkhead during transport and installation. An alternative method for affixment is to heat weld the bulkheads directly onto the plastic film.

The air outlet section was then welded using a straight-line ribbon impulse welder set at an appropriate amount of time and pressure for the materials used as shown in FIG. 5A. A hole was cut in the outer plastic sheet at the spot illustrated in FIG. 5A and a bead of high temperature hot glue was placed around the edge of that hole. The plate port (FIG. 5B) was then affixed over that hole and held in place for a few seconds to ensure equal distribution of glue. This plate port is the air outlet for the photobioreactor chamber. Other affixment methods, including welding and adhesives, can be used to attach the plate port to the plastic film.

The final slanted welds were made at the terminal ends of the photobioreactor chamber at this point, using a the ribbon straightline welder set at the appropriate amount of time and pressure for the materials used. These final welds created the terminal ends and the last two tubes as shown in FIG. 6.

An air inlet tube comprised of hard plastic 1 centimeter in internal diameter and 10 centimeters in length was then affixed at the entrance to the air tube (FIG. 7). To do so, a flap of plastic was cut from that section (four layers of plastic were being cut at this point) in the form of a rectangle (FIG. 7). The cut terminated just beyond the end of the vertical weld. The air inlet hard plastic tube was inserted 7.5 centimeters into the air tube. A liberal amount of high temperature hot glue was applied to the interface between the hard plastic tube and the photobioreactor chamber and held gently in place for five seconds to ensure that it was sealed.

Excess plastic was then cut off around the photobioreactor as shown in FIG. 8. This resulted in a single completed photobioreactor chamber. It should be noted that in the overall photobioreactor system, only some photobioreactor chambers will require 7 bulkheads for sensor measurements and sample collection. Most bags will only require the air inlet tube, plate port for air outlet and two bulkhead fittings: one for liquid inlet and one for liquid outlet.

The photobioreactor chambers were paired and a final heat seal was run across the length of the two bags to join them at the top (FIG. 9). The paired photobioreactor chambers were then ready to be placed in the photobioreactor system.

The photobioreactor chamber material should be flexible, durable and transparent. In a preferred embodiment, the chamber material was comprised of a multi-layer composite polymer, comprising one layer of nylon plastic film bonded on either side with a tie layer of bonding agent and a layer of low density polyethylene (LDPE). The bonding agent adhered to both the LDPE and nylon when subjected to heat and pressure.

The nylon-LDPE plastic film can vary in thickness, depending on the species of photosynthetic microorganism and the corresponding level of turbulence required for light cycling, shear-stress limitations, etc. A preferred example of the LDPE-nylon film is 3.5 thousandths of an inch thick. At this thickness, a moderate amount of turbulence within the photobioreactor chamber would have little effect on the film's structural integrity. Other thicknesses which may be utilized in the practice of exemplary embodiments are 1.5 thousandths of an inch, 2.5 thousandths of an inch, 5 thousandths of an inch, 7 thousandths of an inch and 10 thousandths of an inch. These thicknesses provide sufficient structural integrity for varying levels of turbulence within the photobioreactor chamber.

Other examples of plastic film which can be used are single layer LDPE, linear low density polyethylene (LLDPE), fiber-reinforced LDPE, high-density polyethylene (HDPE), poly vinyl chloride (PVC), polypropylene (PP), single-layer nylon, polyester (PET), ethylene vinyl acetate (EVA), polyvinyledine chloride (PVLC), ethylene vinyl alchohol (EVA), polystyrene (PS) and any other transparent plastic film known in the art. Additionally, any combination of the above polymer films may be used to create a multi-laminate hybrid polymer. Thicknesses of the above-described films will vary according to the species of photosynthetic organism chosen to be grown in the photobioreactor system. Preferably, the thickness chosen is the minimum thickness allowable for structural integrity to reduce the cost of the bag material in constructing the photobioreactor.

A preferred embodiment for joining the sheets of plastic film together uses a constant-heat-welder set at the appropriate time, pressure and temperature for the materials used. Press times depend on the thickness of plastic film, material used and number of layers.

The impulse welders used in exemplary embodiments to join plastic films together comprise a 30 volt impulse welder run through a 68.5 centimeter long NiChrome ribbon that was one thousandth of an inch thick. One non-limiting exemplary setting to join together two sheets of 5 thousandths of an inch Nylone-LDPE five-layer polymer film was at a pressure of 50 pounds-per-square-inch for a period of 4 to 10 seconds.

When filled with growth medium, the photobioreactor panel inflated and the areas between the parallel vertical heat welds bulge out, creating a series of tubes whose tops and bottoms were open. Thus the photobioreactor panel has a continuous flow through it, while also having a rigid structure due to the structural support provided by the heat welds and the higher pressure inside the photobioreactor chamber in relation to the pressure of the surrounding water.

The growth medium was kept at a level slightly below the "zig" heat weld that was below the topmost heat weld. Air was pumped into the air tube at a pressure that was sufficient to keep growth medium from entering the sealed air tube, while bubbles were forced out of each puncture. The bubbles then rise through the medium and burst at the air-liquid interface.

The upper air pocket (which was fed by the sparging bubbles) provided positive buoyancy that adds to the structural integrity of the photobioreactor panel. Thus it is important that the upper air pocket be greater in volume than the sealed air tube, which will otherwise compete to buoy the panel. If an external water basin is not used, the internal hydrostatic pressure of the growth medium inside the photobioreactor chamber may be increased to maintain the structural rigidity of the photobioreactor chamber.

Additional heat welds can be added to the parallel vertical tubes in the form of dimples as means to create a longer course for the bubbles as they rise upwards. This aids in lengthening bubble retention and thus maximizing gas exchange per given amount of sparged air.

Another method of creating a desired bubble course is to apply a heat gun to the exterior of the tubes in order to create deformation in the plastic that resembles wrinkling. These wrinkles also slow down the ascent of the bubbles and add to the amount of gas exchange per given amount of sparged air. This effect can also be created by vacuum-forming the wrinkles into the plastic film.

The photobioreactor chambers were attached together in pairs (FIG. 9) that were arranged in a triangular shape in cross-section (FIG. 10) and were placed inside a water basin for thermal regulation and structural support. The water basin was surrounded by an external perimeter wall as described above (Paragraphs 0050-0051). Pumps, sensors and control systems were integrated into the system as described above in the Detailed Description.

Example 2

Algal Culture

The exemplary photobioreactor described in Example 1 was inoculated with *Nannochloropsis occulata, Nannochloropsis* sp., *Tetraselmis suecica, Tetraselmis chuii, Chlorella salina*, or *Dunaliella tertiolecta*. The *Dunaliella tertiolecta* algal culture was cultivated and grown in the photobioreactor system. Cell densities of up to but not limited to 45 million cells per milliliter (1.5-2.3 g/L) were achieved for *Dunaliella tertiolecta*.

Algae grown in a different photobioreactor with similar characteristics were harvested and lipids were extracted from the algae. The triglycerides were converted into biodiesel using a batch transesterification process.

Example 3

Enhanced Lipid Production by Nutrient Limitation

*Tetraselmis suecica* was grown for 5-8 days in f/2 medium with an additional 0.5 g-2 g of $NaHCO_3$/L, pH 7.2-7.5 to the maximum cell density in a range of $10\text{-}62 \times 10^6$ cells/mL. The dry weight was 1.4-11 g/L, respectively under continuous agitation with $CO_2$ (1-2%). $NaNO_3$ and $NaH_2PO_4 \cdot H_2O$ were added as needed. After reaching maximum cell density no additional $CO_2$ was provided. Neutral lipids were formed in 24 h after reaching maximum cell density and discontinuation of $CO_2$ supply. pH rose from 7.5 to 10-11. Rising of pH is an indicator of lipid production.

The dynamics of lipid formation after 24 h was monitored using fluorescence measurements with Nile Red. Algal samples were diluted to an optical density of 0.1 at wavelength of 750 nm. 35 µL of Nile Red in DMSO was added to 3.5 mL of the dilute algae to the final concentration of 1 µg/ml. The sample was thoroughly mixed and read after five minutes incubation (a longer incubation time might be necessary for other species) at room temperature using excitation wavelength 525 nm and emission in a range from 540 to 800 nm using a Perkin Elmer LS55 Fluorometer. Neutral lipids emit at 580-600 nm. The types of lipids that accumulated were analyzed by thin layer chromatography. The amount of total fatty acid methyl esters were confirmed by gas chromatography.

What is claimed is:

1. A closed system photobioreactor comprising one or more closed photobioreactor chambers surrounded by a water basin over a ground surface, said photobioreactor capable of growing photosynthetic microorganisms, wherein one or more of the one or more closed photobioreactor chambers forms an angle with respect to the ground surface, from a cross-sectional view, to extend a surface area of the photobioreactor in order to increase photosynthetic efficiency by increasing exposure of the photobioreactor chambers to diffuse light.

2. A photobioreactor comprising or more photobioreactor chambers surrounded by a water basin, said photobioreactor capable of growing photosynthetic microorganisms, wherein the one or more photobioreactor chambers comprise a flexible, transparent plastic or composite film, and wherein structural support to the photobioreactor chambers is provided by the water in the water basin, positive buoyancy air pockets in the photobioreactor chambers and/or structural heat welds in the plastic or composite film, wherein the chambers are placed at an angle to each other and affixed at their tops and bottoms to neighboring chambers, to create an accordion shape from a cross-sectional view.

3. A closed system photobioreactor comprising one or more closed photobioreactor chambers surrounded by a water basin, said photobioreactor capable of growing photosynthetic microorganisms, wherein the photobioreactor is designed to increase photosynthetic efficiency by providing diffuse light to the photobioreactor chambers, the photobioreactor further comprising a perimeter wall surrounding the water basin, a bottom liner below the water basin and a top layer of plastic above the water basin to decrease water loss from the water basin.

4. The photobioreactor of claim 3, wherein the water in the water basin provides a thermal mass to decrease fluctuations in temperature of the photobioreactor chambers.

5. The photobioreactor of claim 1, wherein the photobioreactor chamber comprises a bottom layer and a top layer of plastic film that are joined together, with an air pocket at the top of the chamber to provide positive buoyancy, wherein the shape of the photobioreactor chamber is maintained by structural tension.

6. The photobioreactor of claim 5, wherein the air pocket collects oxygen produced by photosynthesis and wherein the oxygen enriched air is collected to provide increased efficiency of combustion in a power plant or combustion chamber.

7. The photobioreactor of claim 3, wherein the top layer of plastic contains a dye, coating or additive to block the transmission of some or all ultraviolet or infrared light, while allowing transmission of visible light to support photosynthesis.

8. A photobioreactor system comprising:
a photobioreactor at least partially surrounded by a water basin, the photobioreactor capable of growing photosynthetic microorganisms, the photobioreactor at least partially constructed of a flexible, transparent plastic or composite film,
wherein a cross-sectional shape of the photobioreactor along at least a portion of a length of the photobioreactor has a longest dimension which forms a nonzero angle with respect to a top surface of water in the water basin, thereby increasing exposure of the photobioreactor to diffuse light.

9. The photobioreactor system of claim 8, wherein a size and a shape of the photobioreactor are configured to be selectively regulated by controlling a pressure within the photobioreactor.

10. The photobioreactor of claim 8, wherein the nonzero angle is sixty to ninety degrees.

11. The photobioreactor of claim 8, wherein structural support to the photobioreactor is provided by the water in the water basin and one or more positive buoyancy air pockets in the photobioreactor.

12. The photobioreactor of claim 8, wherein structural support to the photobioreactor is provided by one or more of: the water in the water basin, one or more positive buoyancy air pockets in the photobioreactor, and structural heat welds in the flexible, transparent plastic or composite film.

* * * * *